(12) United States Patent
Gauthier et al.

(10) Patent No.: US 8,714,058 B2
(45) Date of Patent: May 6, 2014

(54) ELECTRONIC TORQUE WRENCH

(71) Applicants: Michael T. Gauthier, Grafton, WI (US); Austin R. S. Braganza, Milwaukee, WI (US); Ronald Fedder, Germantown, WI (US); Dean Jeutter, Grafton, WI (US); Stacy Gauthier, Grafton, WI (US)

(72) Inventors: Michael T. Gauthier, Grafton, WI (US); Austin R. S. Braganza, Milwaukee, WI (US); Ronald Fedder, Germantown, WI (US); Dean Jeutter, Grafton, WI (US); Stacy Gauthier, Grafton, WI (US)

(73) Assignee: Gauthier Biomedical, Inc., Grafton, WI (US)

( * ) Notice: Subject to any disclaimer, the term of this patent is extended or adjusted under 35 U.S.C. 154(b) by 0 days.

(21) Appl. No.: 13/915,395

(22) Filed: Jun. 11, 2013

(65) Prior Publication Data

US 2013/0291694 A1    Nov. 7, 2013

Related U.S. Application Data

(63) Continuation of application No. 13/110,446, filed on May 18, 2011, now Pat. No. 8,485,075.

(60) Provisional application No. 61/345,817, filed on May 18, 2010.

(51) Int. Cl.
*B25B 23/142* (2006.01)
*B25B 23/14* (2006.01)

(52) U.S. Cl.
CPC ............. *B25B 23/14* (2013.01); *B25B 23/1425* (2013.01)
USPC ........................................... 81/479; 81/177.5

(58) Field of Classification Search
USPC ......................................... 81/467, 479, 177.5
See application file for complete search history.

(56) References Cited

U.S. PATENT DOCUMENTS

| 4,324,158 | A | * | 4/1982 | Le Roy ............................. 81/60 |
| 5,207,697 | A | * | 5/1993 | Carusillo et al. .............. 606/167 |
| 5,476,014 | A | * | 12/1995 | Lampe et al. ............... 73/862.23 |
| 6,070,506 | A | * | 6/2000 | Becker .............................. 81/479 |
| 6,439,086 | B1 | * | 8/2002 | Bahr ................................ 81/467 |
| 6,487,943 | B1 | * | 12/2002 | Jansson et al. .................. 81/475 |
| 6,981,436 | B2 | * | 1/2006 | Becker et al. ................... 81/479 |
| 7,021,180 | B2 | * | 4/2006 | Crane ............................... 81/467 |
| 7,172,561 | B2 | * | 2/2007 | Grinberg ........................ 600/587 |
| 7,272,999 | B2 | * | 9/2007 | Cutler et al. .................... 81/475 |
| 7,334,509 | B1 | * | 2/2008 | Gao et al. ........................ 81/475 |
| 7,430,945 | B2 | * | 10/2008 | Gauthier et al. ................ 81/467 |
| 7,469,619 | B2 | * | 12/2008 | Anjanappa et al. ............. 81/479 |
| 7,650,821 | B2 | * | 1/2010 | Gauthier et al. ................ 81/473 |
| 7,740,628 | B2 | * | 6/2010 | Hoegerle et al. ............... 606/27 |
| 7,762,164 | B2 | * | 7/2010 | Nino et al. ...................... 81/475 |
| 7,913,594 | B2 | * | 3/2011 | Gauthier et al. ................ 81/467 |
| 7,938,046 | B2 | * | 5/2011 | Nino et al. ...................... 81/475 |

(Continued)

*Primary Examiner* — David B Thomas
(74) *Attorney, Agent, or Firm* — Boyle Fredrickson, S.C.

(57) ABSTRACT

A torque wrench for use in driving fasteners is provided. The wrench includes an electronics unit disposed within a body of the wrench that is capable of sensing and measuring the torque applied to a fastener by the wrench and providing an output of the level of torque to the user. The electronics unit is also disposed within a barrier in the body that isolates the unit from the exterior environment around the wrench. The data sensed by the electronics unit can be utilized to provide feedback to the user regarding the operation of the wrench, and to monitor the overall operation of the wrench for calibration purposes, among other functions. During use, the wrench can provide the user with visual, audible and tactile feedback regarding the operation of the device relative to stored maximum torque values stored in the electronics unit.

15 Claims, 19 Drawing Sheets

(56) References Cited

U.S. PATENT DOCUMENTS

| | | | |
|---|---|---|---|
| 8,037,790 B2 * | 10/2011 | Gauthier | 81/467 |
| 2003/0114860 A1 * | 6/2003 | Cavagna et al. | 606/104 |
| 2004/0134316 A1 * | 7/2004 | Loper | 81/467 |
| 2005/0268750 A1 * | 12/2005 | Bruce et al. | 81/52 |
| 2006/0156874 A1 * | 7/2006 | Hsieh | 81/467 |
| 2006/0179981 A1 * | 8/2006 | Cutler et al. | 81/475 |
| 2008/0006130 A1 * | 1/2008 | Hsieh | 81/467 |
| 2008/0016990 A1 * | 1/2008 | Rinner | 81/467 |
| 2009/0178519 A1 * | 7/2009 | Hsieh | 81/467 |
| 2009/0249924 A1 * | 10/2009 | Lin | 81/479 |
| 2011/0314973 A1 * | 12/2011 | Tsai | 81/60 |
| 2012/0042754 A1 * | 2/2012 | Chen | 81/121.1 |

* cited by examiner

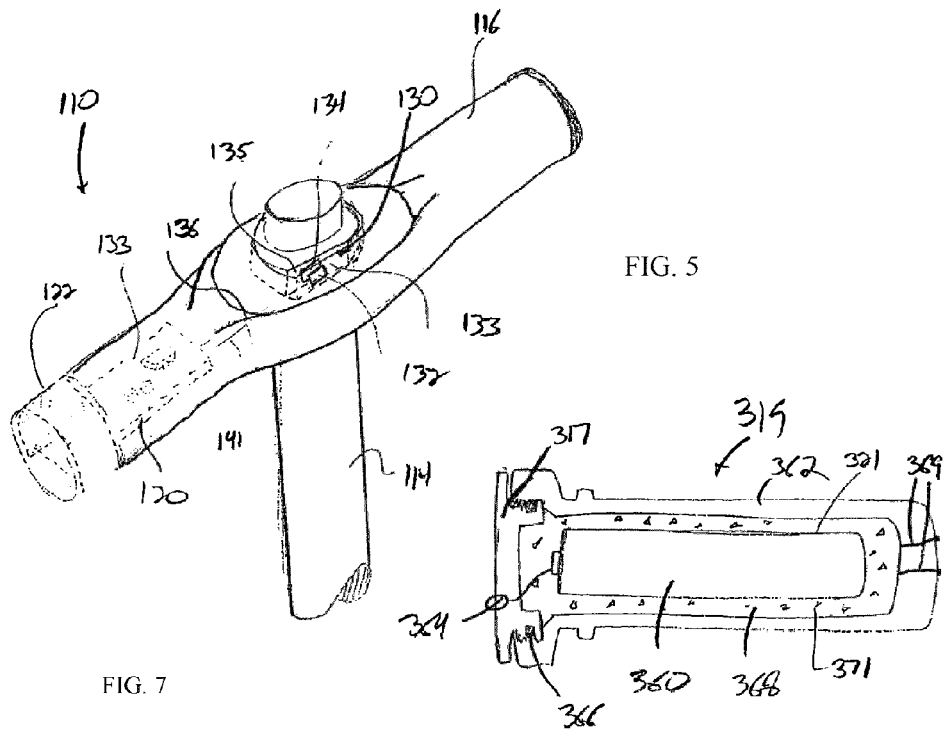
FIG. 5
FIG. 7
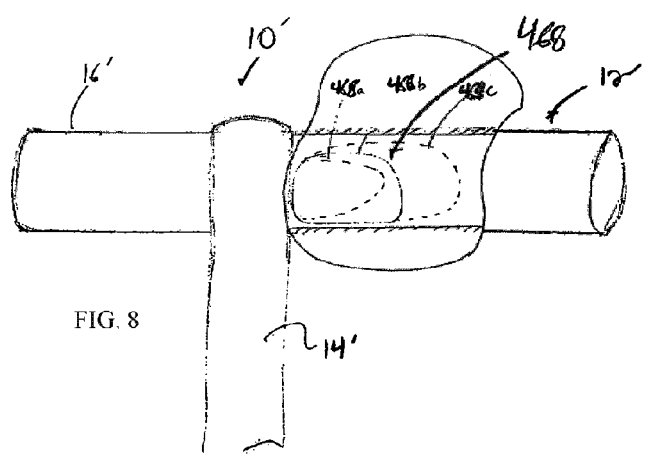
FIG. 8

ELECTRONIC TORQUE WRENCH

CROSS-REFERENCE TO RELATED APPLICATIONS

This application claims priority as a continuation application from U.S. patent application Ser. No. 13/110,446 filed May 18, 2011, which claims priority from U.S. Provisional Application Ser. No. 61/345,817, filed on May 18, 2010, the entirety of which are each hereby expressly incorporated herein.

FIELD OF THE INVENTION

The present invention relates to tools, and more specifically to tools including electronic measuring and display device for providing indication of the forces being applied by the tools.

BACKGROUND OF THE INVENTION

Often, fasteners used to assemble performance critical components are tightened to a specified torque level to introduce a "pretension" in the fastener without damaging the substrate in which the fastener is positioned. As torque is applied to the head of the fastener, beyond a certain level of torque the fastener begins to stretch. This stretch results in the pretension in the fastener which then holds the components together. A popular method of tightening these fasteners is to use a torque wrench. Accurate and reliable torque wrenches help insure the fasteners are tightened to the proper torque specifications.

Torque wrenches vary from simple mechanical types to sophisticated electronic types. Mechanical type torque wrenches are generally less expensive than electronic ones. There are two common types of mechanical torque wrenches, beam and clicker types. With a beam type torque wrench, a beam bends relative to a non-deflecting beam in response to the torque being applied with the wrench. The amount of deflection of the bending beam relative to the non-deflecting beam indicates the amount of torque applied to the fastener. Clicker type torque wrenches work by preloading a snap mechanism with a spring to release at a specified torque, thereby generating a click noise. Other types of mechanical torque wrenches include indicating, ratcheting, torque limiting, in-line and beam styles of torque wrenches. In an indicating wrench, torque value is measured and displayed on a scale. In a torque limiting wrench, the wrench will drive the fastener until a preset torque value is reached at which point the wrench will slip and cease to transmit the torque applied. In a ratcheting mechanism wrench, in order to drive a fastener into a substrate such as wood or bone it is necessary to rotate the fastener through multiple rotations about its axis. For a hand held tool, in order to drive fasteners, typically the user will have to change their grip or change hands in order to keep driving the fastener due to the limitation of the range of motion of the bones joint in a human hand, which occurs at approximately 100 to 180 degrees depending on the person. A ratcheting mechanism in a fastener driver tool allows the user to rotate the instrument in the opposite direction to the torque being applied without lifting or otherwise disengaging the device driving bit from the fastener and without lifting the hand off the device or changing hands. With a ratcheting mechanism in the tool the user can rotate the tool and drive the fastener through as many degrees of rotation as their hand allows and then ratchet the driving tool in the opposite direction so as to be able to drive the fastener through as many degrees without lifting the hand off the driving tool.

Electronic torque wrenches (ETWs) tend to be more expensive than mechanical torque wrenches, and more accurate as well. When applying torque to a fastener with an electronic torque wrench, the torque readings indicated on the display device of the electronic torque wrench in a visible manner, such as by a numeric or light indication, and are proportional to the pretension in the fastener due to the applied torque. However, the readings also depend on, among other factors, the under head friction between the head of the fastener and the adjacent surface of the component and the friction between the mating threads. Static friction is greater than dynamic friction. Therefore, when torquing operations are initiated, increased amounts of torque may be required to overcome static friction forces and initiate rotation of the fastener. Therefore, it follows that torque is preferably applied to the fastener in a slow and continuous manner to allow friction forces to stabilize, to help insure accuracy and to help prevent over-torquing, which can result in damage being done to the fastener or the substrate, with extreme cases resulting in destruction of the fastener or substrate. As well, it is often desirable for the user to see both the current torque value (torque being applied at that instant) and the peak torque value (maximum torque applied up to the present instant) simultaneously. However, existing torque wrenches typically display only the current torque value or the peak torque value at any given time.

When a torque wrench is operated in a "tracking mode," the current torque value is displayed and the user therefore does not necessarily get immediate feedback regarding the actual peak torque value to which the fastener may have been subjected. Although with some electronic torque wrenches it is possible to get this information by downloading the data, this action is typically not instantaneous and, therefore, the operator does not get immediate feedback. On the other hand, when operating in a "peak hold mode," the display of the electronic torque wrench typically shows only the maximum torque applied to the fastener up to that time. In the peak hold mode, the user is often ignorant of the current torque level, which can lead to either over or under-torquing the fastener.

Another factor that can affect the accuracy of a reading on an electronic torque wrench is the operating temperature. Strain gages that are used in electronic torque wrenches to measure applied torque are often affected by temperature. Therefore, to obtain accurate torque measurements, it is often necessary to measure the existing temperature and adjust the displayed torque value for a given strain gauge reading.

Regardless of which type ETW is used, torque extensions may be required to tighten fasteners that are in locations that the torque wrench will not reach. One of the most common methods of attaching a torque extension to an ETW is to replace the original drive head with an extension that has its own drive head. Once the extension is inserted, the readings of the ETW must usually be corrected for any change in lever arm length due to the extension. With the extension in place, the actual torque experienced by the fastener will be either higher or lower than what is actually displayed on the ETW, depending on whether the extension extends outwardly or inwardly from the end of the ETW, respectively.

As a result of these and other issues with prior art electronic torque wrenches, it is desirable to develop an electronic torque wrench that addresses these limitations as well as having other user-friendly features to increase the utility of the wrench.

SUMMARY OF THE INVENTION

According to one aspect of the present invention, an electronic torque wrench is provided for engaging a workpiece, the electronic torque wrench including a wrench body with a wrench head disposed on the wrench body, wherein the wrench head is configured to engage the workpiece. A grip handle is disposed on the wrench body opposite the wrench head and a user interface is carried by the wrench body which is also connected to a microprocessor disposed within the handle, or optionally at a location spaced from the handle. The user interface includes a display, and an input device for inputting a preset torque value, all of which are operably connected to the microprocessor. The display can illustrate a peak torque value continuously during operations and/or an applied torque value continuously during operations.

According to another aspect of the present invention, a method is provided of displaying a peak torque value and an applied torque value as a percentage of a preset torque value on a display of an electronic torque wrench during a torquing operation on a workpiece. The method includes the steps of: inputting the preset torque value into the electronic torque wrench, the preset torque value being the maximum torque that is desired to be applied to the workpiece; detecting a current torque being applied to the workpiece; comparing the current torque to an existing peak torque value displayed on the display; displaying the current torque on the digital display as the peak torque value when the current torque exceeds the displayed peak torque value; comparing the current torque to the preset torque value to determine a percentage of the preset torque value that the current torque corresponds to; and displaying the percentage on the display such that the percentage and the peak torque value are displayed simultaneously at all times during the torquing operation.

According to still another aspect of the present invention, a torque wrench is provided with torque adjustment capability, display of desired torque settings, actual torque achieved display, torque measuring capability and optionally a shutoff at a predetermined torque level. The construction of the wrench provides repeatable and accurate torque application without regard to operator capability or operating environment. Among the several features, objects and advantages of the present invention are the provision of an improved torque-applying tool, optionally a torque wrench of portable character, which:

measures applied torque precisely by electronically sensing torque during operation;
allows convenient operator selection of the predetermined torque level and displays the predetermined torque level;
does not require external sensing and control circuits but are instead integrated completely into the tool in a manner to limit the effects of the external environment on the torque wrench;
provides for torque sensing and torque control by electronic feedback;
does not require an external source of electrical power but is instead capable of long-term use solely under battery power;
can be integrated into typical configurations of existing torque wrenches by use of sensing and control elements which will not interfere with normal speed and convenience of operation of the torque wrench;
uses a torque-sensing technology of significant economy and relative simplicity as to make possible for the first time a generation of portable digital torque-responsive, and optionally torque-controlling driving tools; and
provides such torque-responsive, and optionally torque-controlling tools with such economy and simplicity as to be suited for medical use, as well as use in many other technical areas.

According to still a further aspect of the present invention, an electronic torque wrench, system, and method of using the wrench and system is provided for tightening and standardizing the forces associated with a fastener system and for use in other tool systems. In one embodiment, the system includes access to a database of fastener configuration information for various procedures, specifically as they relate to the particular individual on which the procedure is to be performed. Information is provided to the torque wrench. The torque wrench provides verification of the information and verification of application of the information. After use, the tool assembly transfers the information back to the system to provide a historical record of the event.

According to still another aspect of the present invention, the torque wrench system includes a coupling device or coupler. The coupling device receives information from the system and transfers it to the torque wrench. Once the fastener configuration information is received, the torque wrench is removed from the coupler and is used to establish torque settings for use in the fastener torque process. Verification of the tightening process is recorded at the torque wrench and transmitted back to the coupler. The coupler then transfers the information to the system.

According to still a further aspect of the present invention, the system includes a driving device management server which communicates with the microprocessor. The coupler is connected to the server to collect information about the procedure/subject from the server. The device management server then delivers corresponding fastener configuration information to the coupler for transfer to the torque wrench. The torque wrench utilizes the information in the fastener tightening process. Verification of the information can be recorded at the tool and transferred back to the coupler when the torque wrench is placed in connection with the coupler. Information transferred to the coupler can be transmitted to the management server for verification, transaction completion and storage.

According to still another aspect of the present invention, the data regarding the use of the torque wrench in performing the fastener tightening procedure or process stored in the microprocessor can be transferred to the coupler and/or server to record the usage of the torque wrench. This data can be stored in the server for use in determining the necessary calibration for the tool, based on various parameters such as the number of uses of the tool, and the overall length of time of use of the tool, among others.

According to still a further aspect of the present disclosure, the torque wrench is formed with a gas and moisture barrier within the wrench around the electronic components or unit and optionally the power supply to enable the wrench to remain unaffected by the external environment around the wrench, such as when the wrench is sterilized by autoclaving, for example.

Other aspects, features and advantages of the present invention will be set forth in part in the description which follows and the accompanying drawings, wherein the embodiments of the disclosure are described and shown, and in part will become apparent upon examination of the following detailed description taken in conjunction with the accompanying drawings.

BRIEF DESCRIPTION OF THE DRAWINGS

The drawings illustrate the best mode currently contemplated of practicing the present disclosure.

In the drawings:

FIG. 5 is an isometric view of a third embodiment of an electronic driving tool constructed according to the present disclosure;

FIG. 7 is a cross-sectional view of power cell component of the tool of FIG. 1;

FIG. 8 is a cross-sectional view of a temperature compensation bladder or use with the tool of FIG. 1;

DETAILED DESCRIPTION OF THE INVENTION

Reference will now be made in detail to various embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Figure 1:
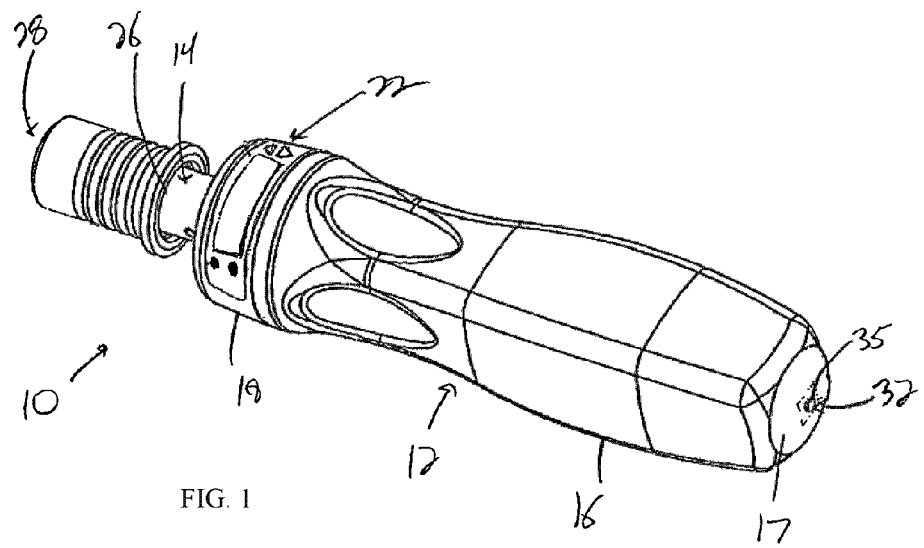
FIG. 1 is an isometric view of a first embodiment of an electronic driving tool constructed according to the present disclosure.
Figure 2:
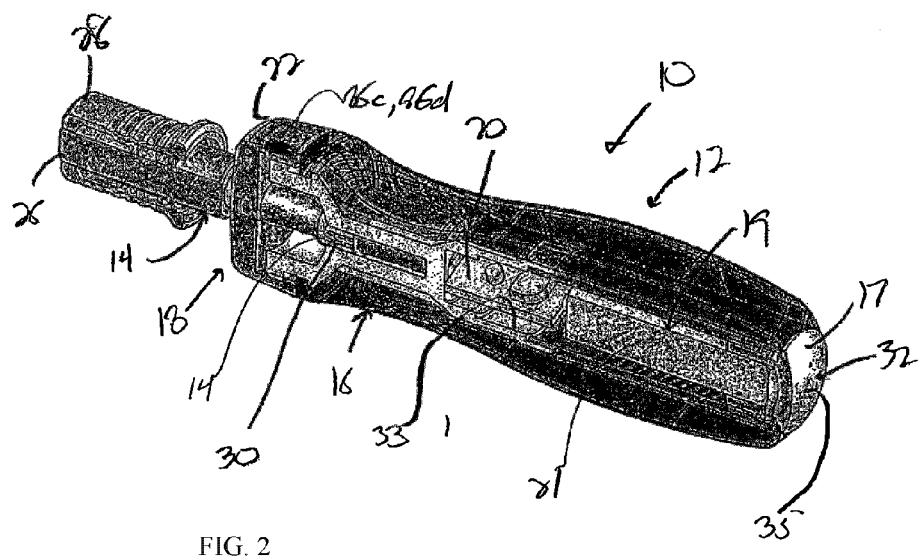
FIG. 2 is a cross-sectional view along line 2-2 of FIG. 1.

Referring now to FIGS. 1 and 2, an in-line electronic torque wrench 10 in accordance with the present disclosure is shown. The electronic torque wrench 10 includes a wrench body 12, a ratchet/wrench shaft 14, a grip handle 16, a housing 18, a battery assembly 19 including battery 21, and an electronics unit 20 with a user interface or display 22 that is operably connected to the battery assembly 19. In the illustrated embodiment, wrench body 12 is of tubular construction, made of steel or other rigid material, and receives shaft 14 at a first end and a power supply or battery assembly 19 at a second end, secured therein by an end cap 17. Housing 18 is mounted therebetween and carries electronics unit 20. Additionally, in the illustrated embodiment the handle 16 is formed around the housing 18, such as from an elastomeric material that can be molded in a suitable manner to conform to the desired shape for the wrench 10.

As shown, a front end 26 of shaft 14 includes an adapter 28 connected to a suitable ratcheting mechanism (not shown) such as that shown in U.S. Pat. No. 7,413,065, which is incorporated by reference herein in its entirety. The adapter 28 is configured to receive variously sized sockets, extensions, etc. The adapter 28 can also be detachably connected to the shaft 14 by any suitable mechanism.

The attachment mechanism for securing the shaft 14 to the body 12 includes a sensor 30 configured to sense the torque or strain exerted by the wrench 10 through the shaft 14 onto a fastener (not shown). The sensor 30 can take any of a number of suitable forms, such as a strain gauge, a Hall sensor, or a piezoelectric sensor, among others.

The sensor 30 is operably connected to the electronics unit 20, and optionally the battery assembly or power supply 19, such that the signal generated by the sensor 30 can be transmitted to the unit 20. Once in the unit 20, which can include a microprocessor (not shown), the unit 20 can utilize the signal for a variety of purposes, such as to calculate a torque value from the signal to provide a real-time indication of the torque applied via the wrench 10 on the display 22 connected to the unit 20.

The operation of the electronics unit 20 and the sensor 30 is controlled by a switch 32 disposed on the body 12, and operably connected between the unit 20 and sensor 30, and the power supply 19 at the opposite end. Thus, the switch 32 enables power to be selectively applied to the unit 20 and sensor 30 as desired.

In the embodiment illustrated in FIGS. 1 and 2, the switch 32 is positioned within the end cap 17 located opposite the adapter 28. The switch 32 is engaged within the cap 34 in a manned that forms a gas and moisture barrier 33 around the switch 32, while leaving and engagement portion 35 of the switch 32 outside the barrier 33. This barrier 33 is also maintained around the battery assembly 19 and electronics unit 20 by the housing 18 and the handle 16, which is in one embodiment formed from an elastomeric material, such as a silicone, disposed at least in part around the housing 18. In this configuration, the barrier 33 formed in the illustrated embodiment by the handle 16, end cap 17 and housing 18 isolates the sensor 30, electronics unit 20 and battery assembly 19 from the exterior of the wrench 10 such that the wrench 10 can be sterilized, such as in an autoclave, for repeated use in medical operations. In another embodiment, the end cap 17 is secured to the handle 16 and housing 18 in a permanent manner, such that the wrench 10 is disposable after the battery assembly 19 becomes depleted, which can be indicated on the display 22.

Further, the display 22 is mounted within the handle 16 on the exterior of the housing 18 such that the material forming the handle 16 forms a gas and moisture impermeable barrier around the display 22, similar to that formed around the battery assembly 19 and the electronics unit 20.

Figure 3:
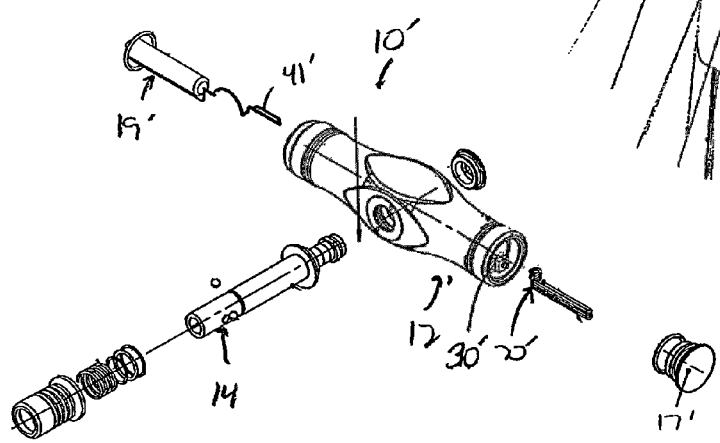
FIG. 3 is an exploded, isometric view of a second embodiment of an electronic driving tool constructed according to the present disclosure.
Figure 4:
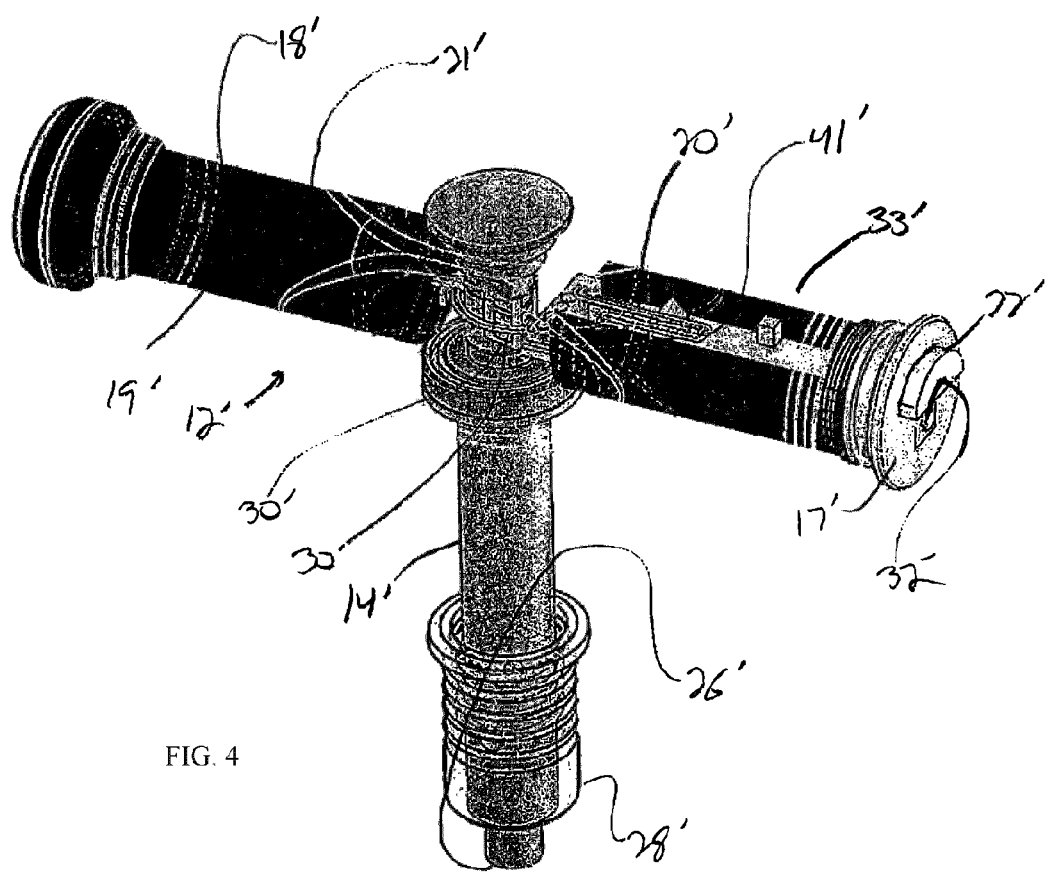
FIG. 4 is an isometric view of the interior components of the tool of FIG. 3.

Referring now to FIGS. 3 and 4, a second embodiment of the wrench 10' is illustrated. In this embodiment, the wrench 10' has a T-shape, with the shaft 14' extending perpendicularly from the body 12' in which is disposed a housing 18', and over which is located a handle 16'. In the illustrated embodiment, the shaft 14' is disposed centrally on the body 12' and extends perpendicularly from the body 12' with the end 26' and adapter 28' spaced therefrom, such that the power source 19' and the electronics unit 20' are disposed on opposite sides of the body 12' and connected to one another by connectors 41', while still contained within the barrier 33'. Alternatively, the shaft 14' can be oriented to one side or the other of the body 12', as desired.

The shaft 14' can be connected directly to the body 12' or to a ratcheting mechanism (not shown) disposed within the body 12'. At the connection of the shaft 14' to the body 12', a sensor 30' is disposed to determine the strain or torque being applied by the wrench 10' through the shaft 14' to a fastener or other substrate (not shown). This embodiment of the wrench 10' can also be formed similarly to that in FIGS. 1 and 2 where the power source 19', electronics unit 20' and display 22' are effectively sealed within the body 12', rendering the wrench 10' disposable when the power source 19' is depleted. Alternatively, the power source 19' for this or any other embodiment can be formed to be wirelessly rechargeable in a known manner, such that the wrench 10' can be formed in a sealed configuration with the barrier 33 enclosing the power source 19', but can be recharged when the power source 19' becomes depleted.

Referring now to FIG. 5, a third embodiment of the wrench 110 is illustrated. The wrench 110 has a T-shape similar to the embodiment of FIGS. 3 and 4, but includes a piezoelectric sensor 130 within the handle 116. The sensor 130 is formed of a first element 132 on a flat surface 133 of the shaft 114 and a second element 134 is disposed on an adjacent flat surface 135 of the body 112. The relative position of the elements 132 and 134 is determined by the electronics unit 120 disposed in the barrier 133, which is connected to the elements 132 and 134 by conductors 136, 141 to receive signals from the elements 132 and 134 for use in operating the display 122.

Figure 6A:
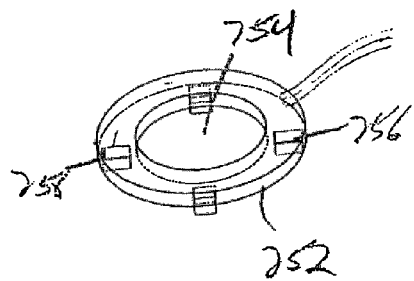
FIGS. 6 and 6A are isometric views of a lighting element utilized with the tool of FIG. 1.
Figure 6:
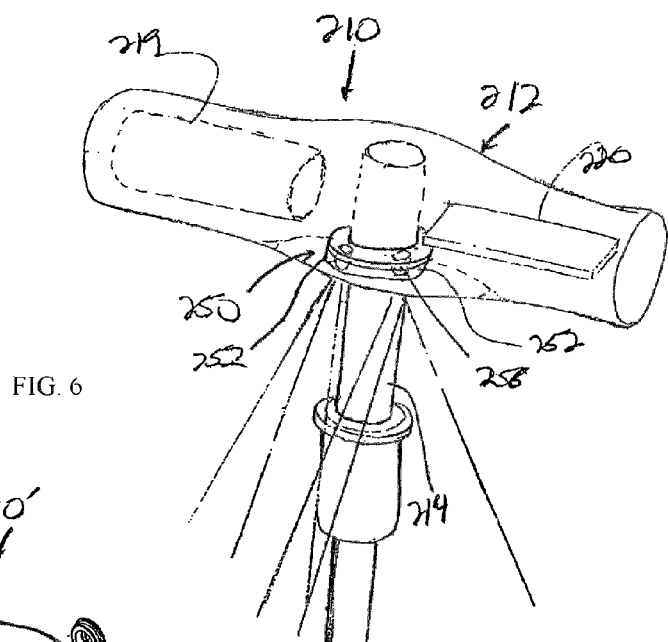

Looking now at FIGS. 6 and 6A, a driving tool or wrench 210 is shown similar to that in FIGS. 3-5, in which the wrench 210 additionally includes a light source 250. The light source 250 is formed with a generally circular housing 252 that has a central aperture 254 that is slightly larger in shape than the shaft 214, such that the housing 252 is positionable around the shaft 214 either immediately adjacent the body 212, or disposed within the body 212, similar to the display 222. In either configuration, the housing 252 includes a number of lighting elements 256 positioned thereon that are operably connected to the power source 219 and optionally the electronics unit 220, either directly or via an intervening member, such as the housing 252 if formed of a conductive material. The lighting elements 256 direct light downwardly from the body 212 along and around the shaft 214 to illuminate the area immediately surrounding the shaft 214, thereby providing a better viewing area for the individual operating the wrench 210.

Referring now to FIG. 7, a power source 319 that can be utilized within the wrench 10,10' is illustrated that includes a battery or power cell 360 positioned within a capsule 362 that is releasably engaged with a cap 317 having a switch 332 therein, such as via a threaded connection. The cap 317 is sealingly engaged with the capsule 362 by a sealing member 366 disposed between the capsule 362 and the cap 317. The power cell 360 or battery 321 is held within the capsule 362 by an insulating material 368, such as a foam 371. The insulating material 368 prevents any inadvertent discharge of electricity from the power source 360 through the capsule 362, as well as insulating the power cell 360 against severe high and low temperature fluctuations, and to encapsulate the power cell 360 to prevent damage due to humidity and immersion in water. To facilitate the passage of power from the cell 360 to the wrench 10,10', such as through the barrier 33, conductors 369 are disposed within the capsule 362 and connect the power cell 360 with the switch 364 and the electronic unit (not shown) disposed within the wrench 10,10' via separate and aligned connectors (not shown) on the wrench b10, 10' that extend though the barrier 33 without breaching the barriers 33.

In FIG. 8, the wrench 10' is shown as additionally including an expandable bladder 468 within the body 12'. The bladder 468 can expand or contract within the body 12' as shown by representations 468a, 468b and 468c in response to changes in the temperature or pressure of the environment in which the wrench 10' is operated to maintain the proper operation of the internal components of the wrench 10'. The bladder 468 continuously creates a neutral pressure in the body 12' to prevent dirt, moisture or other contaminants from being drawn into the body 12' of the wrench 10'. Further, the bladder 468 can assist in maintaining the internal environment within the wrench 10' relatively constant, such that exterior temperature and pressure changes do not significantly affect the operation of the wrench 10' and electronics unit 20'. In addition, the bladder 468 can form a secondary barrier within the wrench 10' around the electronics unit 20' and/or the battery assembly 19'.

Figure 9:
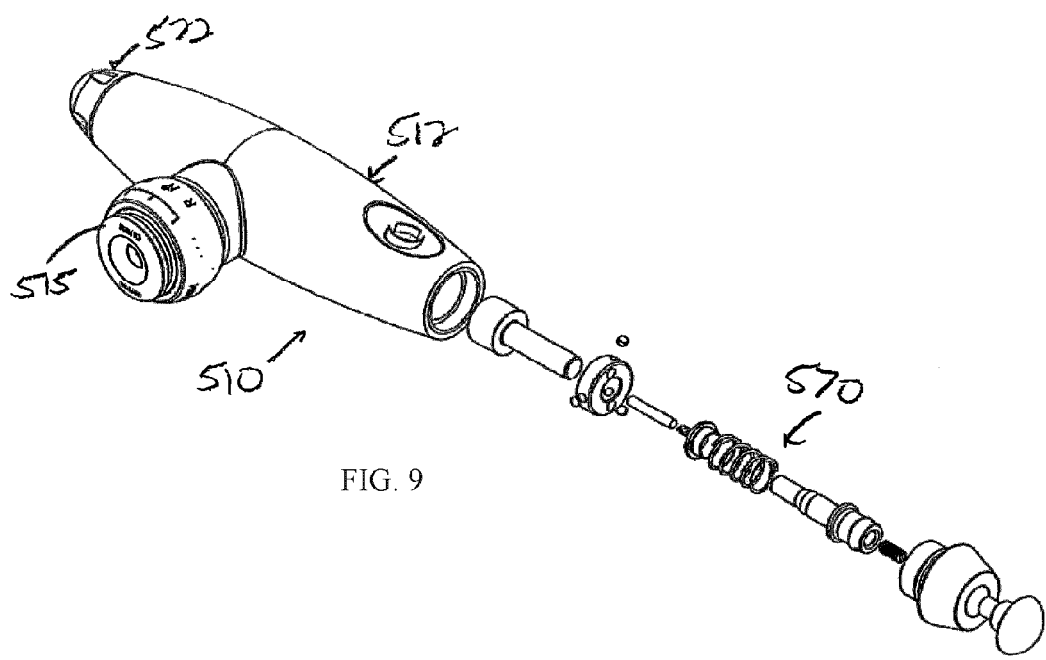
FIG. 9 is an exploded, isometric view of a fourth embodiment of an electronic driving tool constructed according to the present disclosure.

Looking now at FIG. 9, a fourth embodiment of the wrench 510 is illustrated. In the wrench 510, the body 512, in addition to the ratcheting mechanism 515 and other components of the prior embodiments 10 and 10', has a mechanical torque level measuring and/or indication mechanism 570, such as that disclosed in U.S. Pat. No. 7,806,026, incorporated herein by reference in its entirety. The pop-out indication mechanism 570 operates in conjunction with the display 522 to illustrate the particular torque level at which the wrench 510 is being operated.

Figure 10:
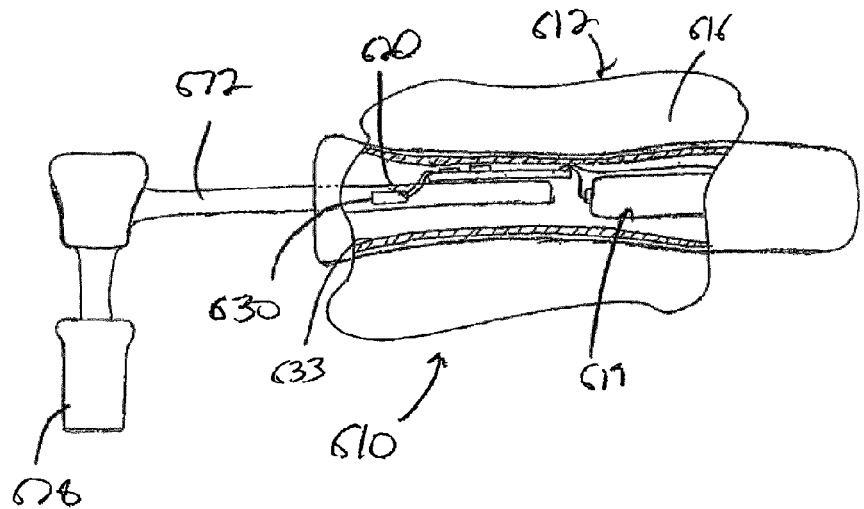
FIG. 10 is a cross-sectional view of a fifth embodiment of an electronic driving tool constructed according to the present disclosure.

Referring now to FIG. 10, a fifth embodiment of the wrench 610 is illustrated in which the wrench 610 is a deflection beam type wrench. The wrench 610 includes a body 612 having a housing 618 optionally forming a part of barrier 633 around the power source 619 and electronic unit 620 in the housing 618 and around which a handle 616 is located. A sensor 630 operably connected to the electronics unit 620 is disposed on a beam 672 engaged with the body 612, and having an adapter 628 attached thereto opposite the body 612. In addition, the beam 672 can include a separable connection (not shown) such that the adapter 628 can be removed from the remainder of the wrench 610 and replaced with another component, such as an adapter with another angular configuration. Other configurations for the wrench 10, 10 are also contemplated, such as a right angle wrench configuration (not shown).

Figure 11A:
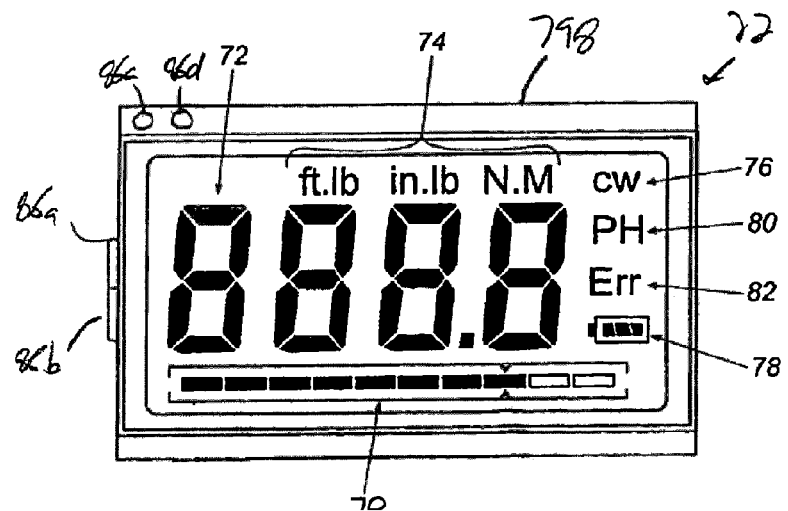
FIGS. 11A-11B are front plan views of the display for the tool of FIG. 1.
Figure 11B:
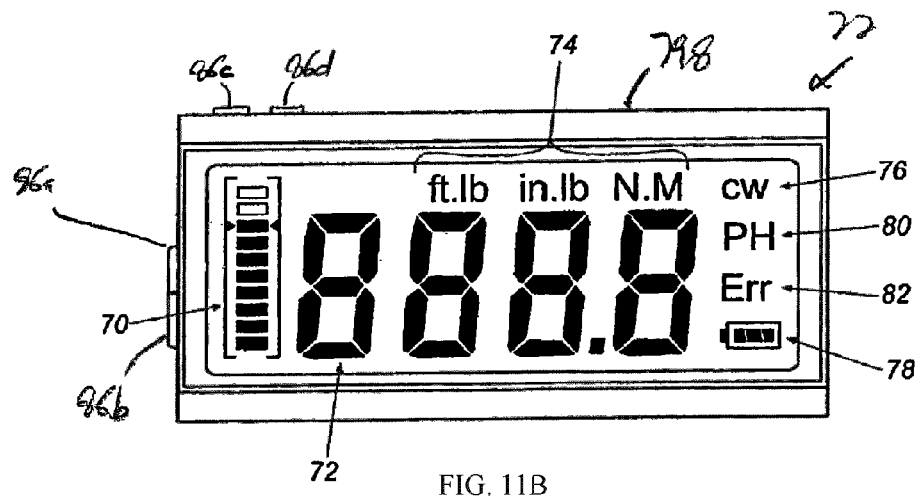

Looking now at FIGS. 11A-11B, a pair of embodiments of the display 22 for the wrench 10 are illustrated. The display 22 can take any suitable form, and can be positioned on the exterior surface of the body 12 for interaction with the individual utilizing the wrench 10, such as in a cut-out section of the housing 18 or handle 16, or can be disposed within the body 12 in an easily viewable location, such as under a transparent section of the handle 16. The display 22 provides various indications to the user of the wrench 10 regarding the operation of the wrench 10, such as, but not limited to, a numerical display 72 of the actual torque being applied in various units 74 (foot-pound, inch-pound, and Newton-meter), a torque level indicator 70, the power level 78 remaining in the power source 19, and a torque direction indicator 76 (clockwise (CW) by default and counterclockwise (CCW) if selected), a peak hold (PH) indicator 80 and/or an error indicator 82 with regard to the operation of the wrench 10.

As shown, current torque level indicator 70 is in the form of a bar graph. The bar graph is shown in two embodiments, horizontal and vertical. In either case, preferably, the bar graph includes a total of ten segments and a frame that encompasses all ten segments. The frame is filled by the ten segments when the preset torque value input by the user is reached. At other times, the frame is only partially filled with segments, and therefore gives a graphical display of approximately how much torque is currently being applied and how much more torque needs to be applied to the fastener to reach the preset torque valve.

As shown, two small arrows are located on opposing sides of the eighth segment. The arrows are graphical indicators to the user that the current torque level is above 75% of the preset torque value. Each segment within the frame represents 10% of the preset torque value, starting from the left or bottom of each bar graph, respectively. For example, if only the first two of segments are displayed, the current torque level is above 15% and below 24% of the preset torque value, and is therefore approximately 20% of the preset torque value. Simultaneously, the digital display also displays the peak torque value applied up until that time in the numeric display. As such, if torque has been applied in a continuously increasing manner, the peak torque value displayed will actually be the same as the current torque value. The decimal point will be displayed depending on which units the user has selected.

In use, the user, rather than focusing on four digit numeric display, views the bar graph of current torque level indicator until the applied torque level reaches approximately 75% to 80% of the preset torque value, depending on the user's comfort level when approaching the preset torque level. At this point, the user changes focus to the numeric display for a precise indication of the current torque being applied as the preset torque value is approached. As discussed, the numeric display shows the peak torque value to which the fastener has been subjected. As such, if the user has "backed off" during the application of torque, the value indicated on numeric display will not change until it is exceeded by the current torque value. The display allows the user to apply torque to the fastener and know both how much torque is currently applied and how much more torque needs to be applied before reaching the target preset torque value.

Alternately, the bar graph display can be used for displaying the peak torque value and the numeric display can be used to display the current torque value. Alternate embodiments include graphical displays other than the previously discussed bar graph, such as a pie chart display in which each of five segments represents approximately 20% of the preset torque value initially selected by the user, a circular dial-type display in which each segment also represents approximately 20% of the preset torque value, an indicator mark at approximately 80% of the preset torque value, or a graphical display that is similar in appearance to a standard dial type analog display wherein a pointer, or needle, indicates the percentage of the preset torque value being applied as it points to graduations positioned about the display. Note, although the number of segments and graduations are shown as representing 20% of the preset torque value, the number may be altered as necessary to indicate a different desired percentage of the preset torque value.

The display 22 can also include one or more user input devices 86 disposed in the body 12. The devices 86 can include a power button 86*a*, a unit selection button 86*b*, increment/decrement buttons 86*c* and 86*d*. Additionally, the display 22 can include light emitting diodes (LEDs) 88*a*, 88*b* and 88*c*. In one embodiment, the light emitting diodes 88*a*, 88*b* and 88*c* are green, yellow and red, respectively, and are activated in response to the torque levels sensed by the electronics unit 20. Also, a speaker 90 for audible signals can also be disposed on the body 12. Additionally, though LEDs 88*a*-88*c* and speaker 90 are shown, the wrench 10 may alternatively or additionally include a device for creating tactile sensation such as a vibration, heating, or cooling. Also, though one possible positioning for the display 22 is shown on the wrench 10, other locations, such as at the end or underside of the body 12 are suitable as well.

Figure 12:
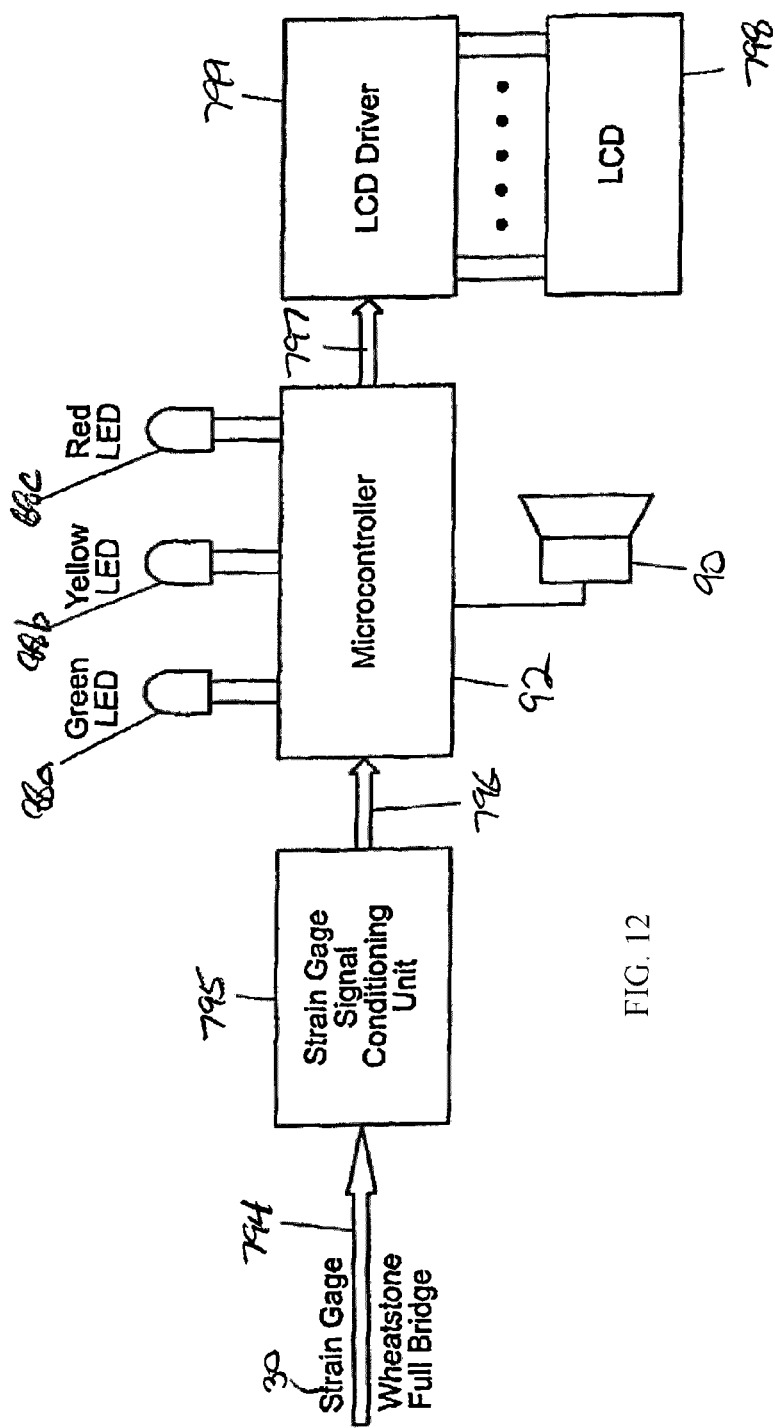
FIG. 12 is a schematic view of a first embodiment of an electronics system of the tool of FIG. 1.
Figure 13:
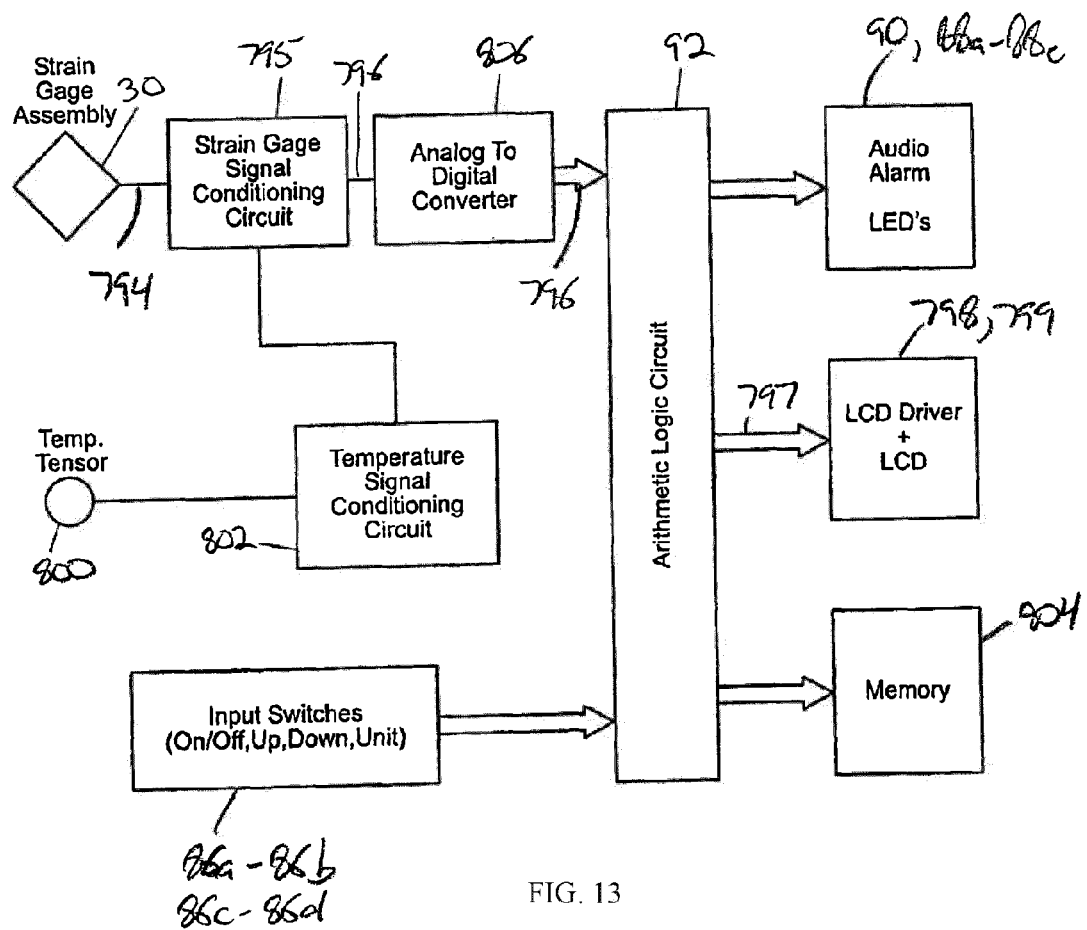
FIG. 13 is a schematic view of a second embodiment of an electronics system of the tool of FIG. 1.

Block diagram representations of a pair of embodiments of the electronics of the wrench 10, including the display 22 and electronics unit 20 with a microprocessor or microcontroller 92, showing various inputs and outputs, are shown in FIGS. 12-13. When electronic torque wrench 10 is used to apply and measure torque, the sensor 30, i.e., the Hall sensor, the piezoelectric sensor, the strain gages of the strain tensor, etc., sense the torque applied to the fastener and send a proportional electrical signal 794 to a signal conditioning unit 795 that amplifies the signal, adjusts for any offset of the signal, and compensates the signal for the current temperature using temperature sensor 800 and conditioning circuit 802. Adjusting for the offset of the signal increases the accuracy of the wrench by compensating the signal for any reading that may be present before torque is actually applied to the fastener. An amplified and conditioned electrical signal 796 is then fed to the microcontroller 92, such as via an analog to digital converter 806 that converts electrical signal 796 to an equivalent torque value in the desired units. Microcontroller 92 sends an electrical signal 797 including the current torque level value and the peak torque value to the display 22, which can include a liquid crystal display (LCD) unit 798, via an LCD driver circuit 799. Preferably, display 22 displays the current torque level value as a bar graph and simultaneously displays the peak torque value as a numeric value, as seen in FIGS. 11A and 11B. Furthermore, microcontroller 92 generates alarm signals in the form of audio signals and light displays of appropriate color once the current torque level value is within a pre-selected range of the preset limit torque value, that are used to operate the LEDs 88*a*-88*c*, and the speaker 90. The LEDs 88*a*-88*c* coincide with the level of torque being applied relative to the preset maximum torque level. Any of the LEDs 88*a*-88*c* are activated, either in a flashing or continuous manner, the user is alerted as to the level of torque being applied via the wrench 10, with the yellow and red LEDs 88*b* and 88*c*, along with the speaker 90 and any associated vibration generator (not shown) indicating to the user that they are approaching or at the torque level where they are over-torquing the fastener.

The switches or buttons 86*a*-86*d* are located on the body 12 adjacent the display 22 and enable the user to adjust the parameters utilized by the electronics unit 20, such as, for example, in setting the minimums and maximum torque levels for the wrench 10.

In addition, the electronics unit 20 can include a memory component 804 that is operably connected to the microprocessor or microcontroller 92 in order to record the information received by the unit 92 during the operation of the wrench 10. In one embodiment, torque values are received by microcontroller 92 on a continuous basis over controlled intervals, which may be specified, for example by the operator of wrench 10 through a user interface, such as the buttons 86a-86d, or other devices that can be operably connected to the microprocessor 92. In any case, in one embodiment, one or more torque measurement values are periodically or continuously stored in memory 800 for later retrieval and/or processing.

Figure 14:
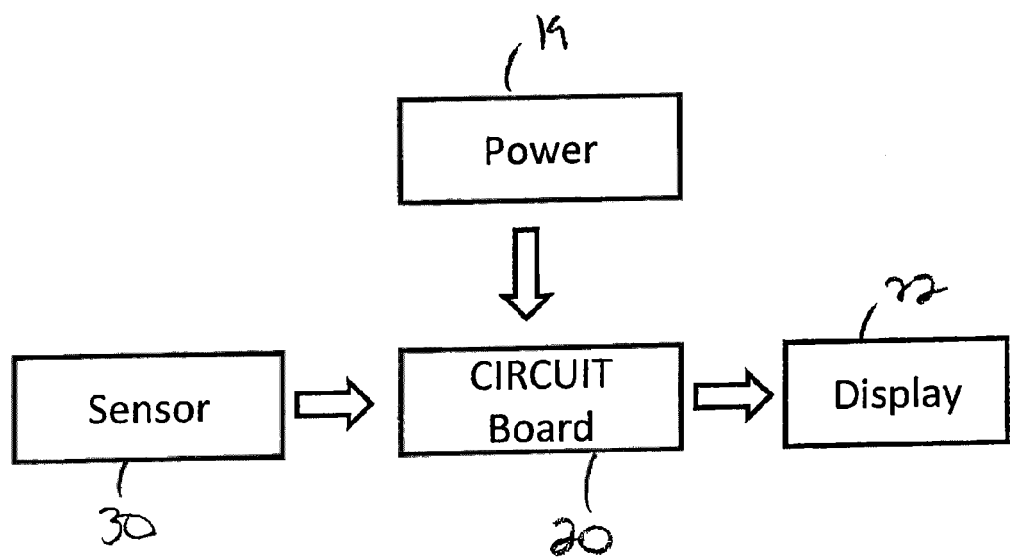
FIG. 14 is a schematic view of a first embodiment of the operating functions of the tool of FIG. 1.
Figure 15:
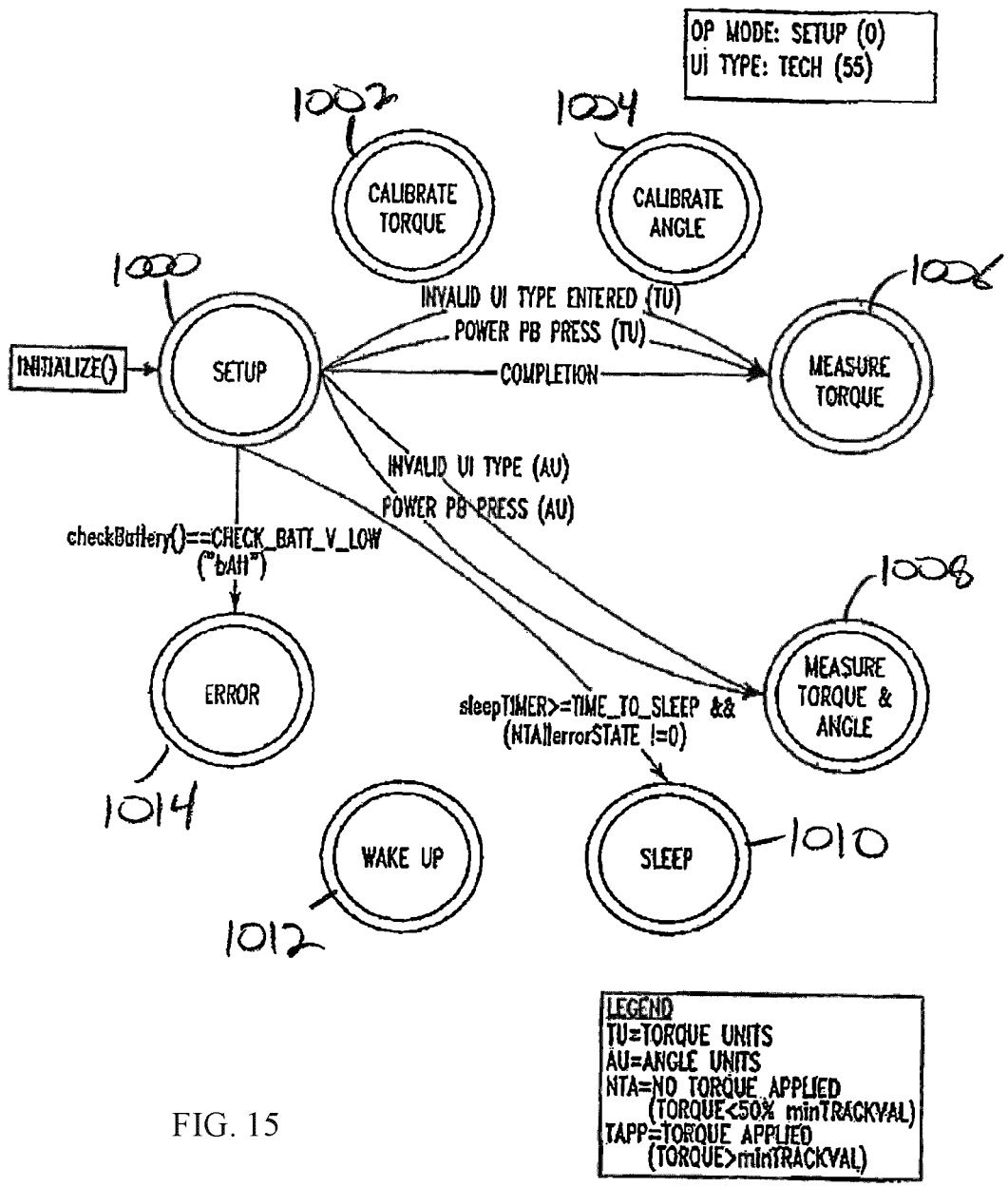
FIG. 15 is a schematic view of a second embodiment of the operating functions of the tool of FIG. 1.

Referring now to FIG. 14-15, the overall functionality of the electronics unit 20 is graphically illustrated. In FIG. 14, in its general functionality, the power supply 19 provides power to the circuit board or electronics unit 20 which receives signals from the sensor 30 for ultimate transmission to the display 22. In FIG. 15, the various functions of the electronics unit 20 are illustrated, namely, an initialization/setup function 1000, a torque calibration function 1002, an angle calibration function 1004, a torque measurement function 1006, a torque and angle measuring function 1008, a sleep function 1010, and wake up function 1012, and an error function 1014 as are each known in the art for various electronic devices.

Figure 16:
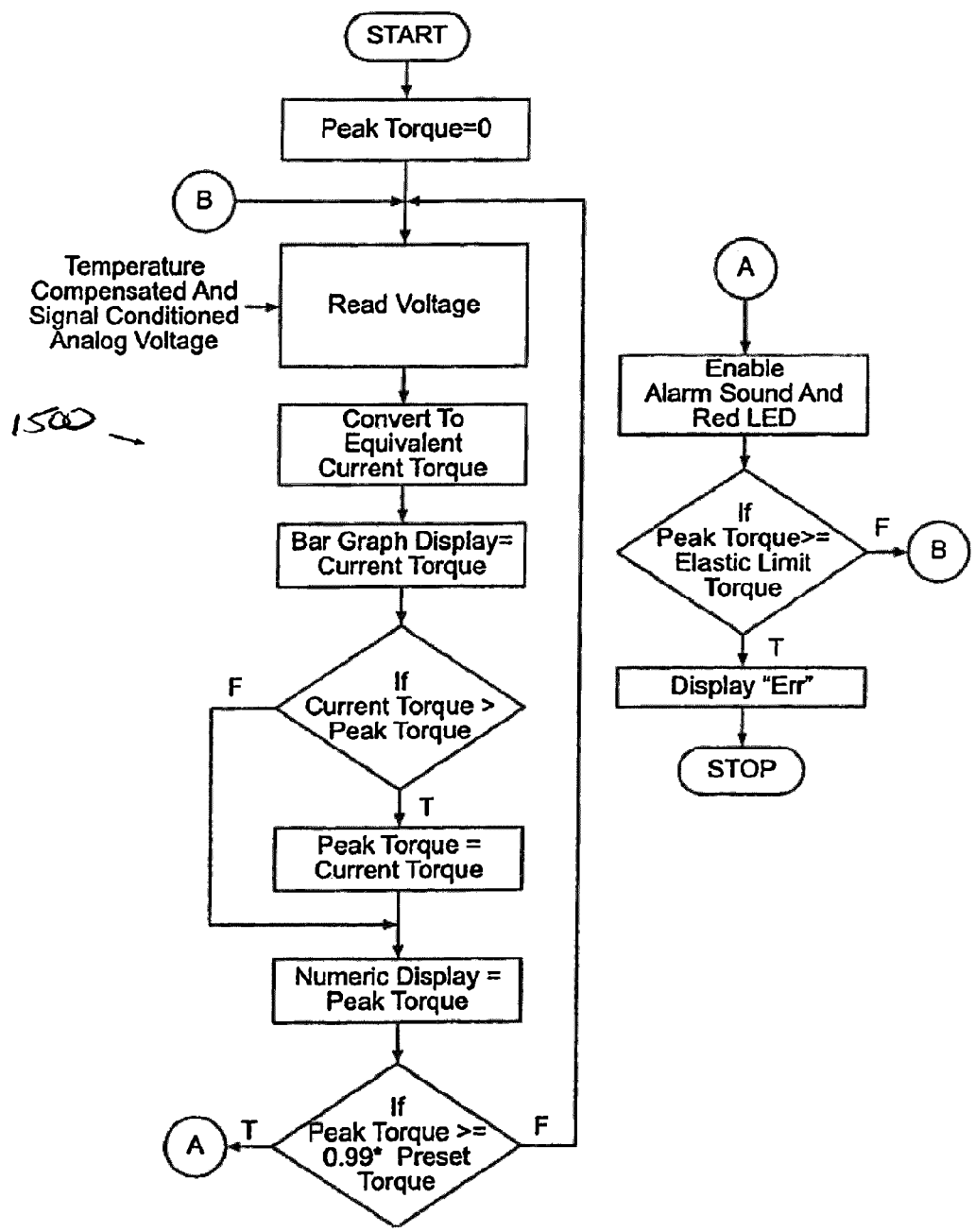
FIG. 16 is a schematic view illustrating the operation of the tool of FIG. 1.

In FIG. 16, a flow chart 1500 of one embodiment of the algorithm used with the electronics unit 20 is shown. Prior to initiating torquing operations, a user inputs a preset torque value into the electronic torque wrench that equals the maximum desired torque to be applied to the fastener, such as by using the buttons 86b-86d. This value is displayed in the display 22 until the user actually applies torque to the fastener, at which time the numeric display switches to displaying the peak torque value. As torque is applied as determined by the sensor 30, microcontroller 92 receives and reads a temperature compensated and signal conditioned analog voltage signal 796 from signal conditioning circuit 795, converts the analog signal to an equivalent digital number, converts the digital number to an equivalent current torque value corresponding to the user selected units, and determines whether the current torque value is a new peak torque value. This is accomplished by comparing the current torque value to the existing peak torque value, and either replacing the peak torque value if it is exceeded (T), or letting it remain if it is not (F). Once both the current torque value and peak torque value are determined, microcontroller 92 sends electrical signal commands to LCD driver circuit 799 to generate appropriate signals to display 22 for updating the readout shown in current torque level indicator and the peak torque value shown in display 22.

In addition, microcontroller 92 operates the display 77 and switches green 88a, yellow 88b, and red 88c LEDs on or off depending on the peak torque value applied to the fastener up until that time. Preferably, green LED 88a comes on as long as the peak torque value is below 75% of the preset torque value and is switched off once the peak torque reaches 75% of the preset torque value. Yellow LED 88b comes on for peak torque values greater than 75% but less than 99% of the preset torque value. Red LED 88c comes on once the peak torque value reaches 99% of the preset torque value and stays on thereafter. The selection of percentage ranges for each color may be programmed, and the percentages at which the LEDs are switched on or off can be changed to suit the specific application. Embodiments are envisioned that include a liquid crystal display device that is capable of displaying multiple colors. This permits the warning LEDs to be replaced by appropriately colored symbols on the LCD. As well, the segments of the bar graphs and graphical displays can be made to have varying colors in order to enhance the warning capabilities for the user.

Once the peak torque reaches the preset torque value, or is within a user selected range, microcontroller 92 can additionally generate electrical signals to generate an alarm sound in speaker 90. A red color backlight (not shown) may coincide with the audible alarm signal, indicating that the preset torque value has been reached. More colors, such as yellow and green, can optionally be added as backlights to further assist the user when approaching the preset torque value. The user is also alerted if the mechanically safe torque value (elastic limit of the strain tensor) has been exceeded, possibly causing the torque wrench to lose proper calibration. This is determined by comparing the peak torque value to the elastic limit torque of the torque wrench. If the safe torque value is exceeded (T), an "Err" message is displayed on error indicator 82 and the unit stops, thus indicating that the electronic torque wrench unit needs calibration before it can be used again.

Figure 17:
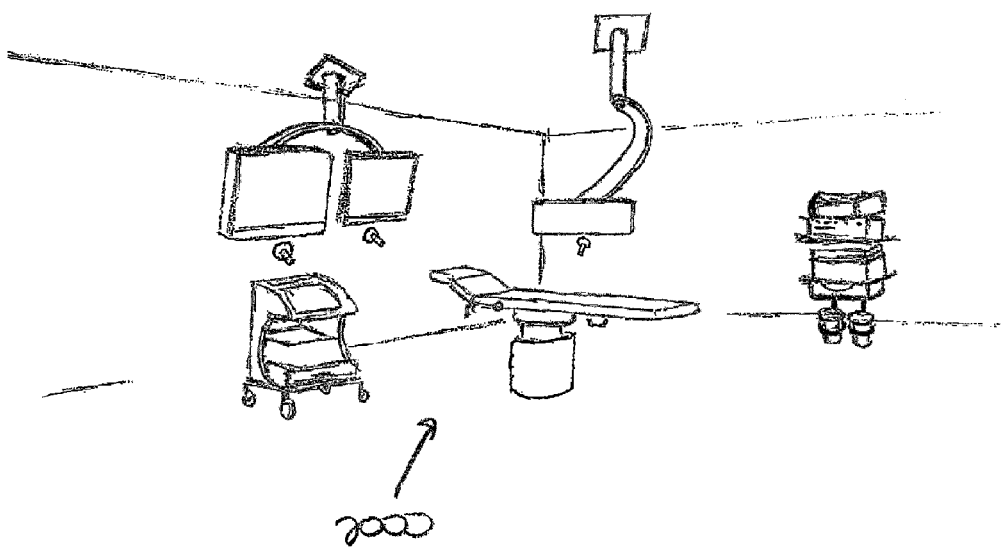
FIG. 17 is a schematic view of a medical suite including a sixth embodiment of an electronic driving tool constructed according to the present disclosure.
Figure 18:
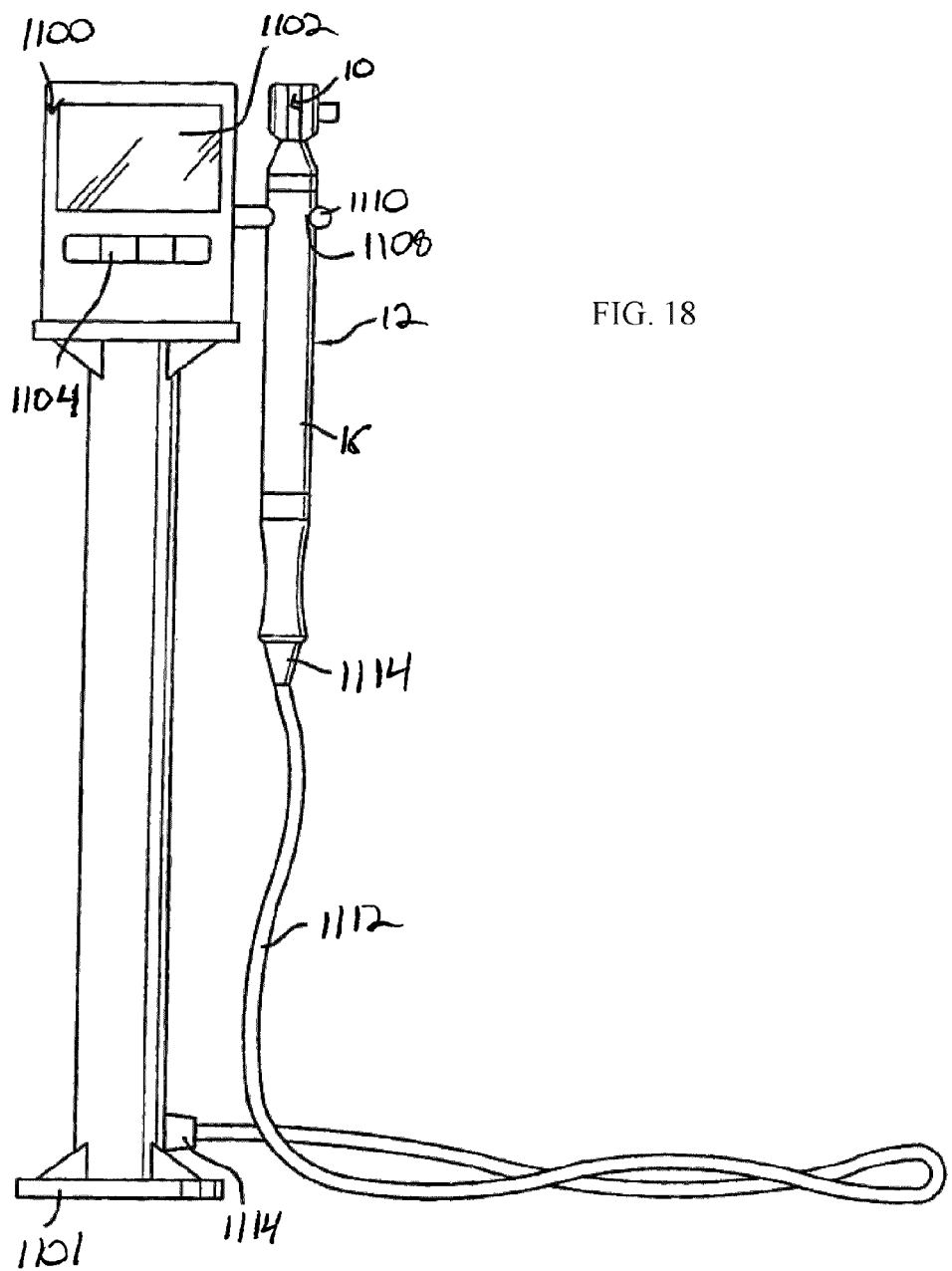
FIG. 18 is a schematic view of the tool of FIG. 17.

As shown in the embodiment of FIGS. 17-18, the wrench 10 can be configured for use in a medical suite 2000 to mate with a control unit 1100 that is supported by a base 1101. Control unit 1100 is configured to communicate with wrench 10 when wrench 10 is docked therein or otherwise engaged therewith. Control unit 1100 include control unit display 1102, control unit buttons 1104 used for inputting commands and interfacing with menus presented on display 1102, and docking section 1106. During docking, wrench 10 is inserted in docking cavity 1108 defined by cradle 1110 and having a width dimension, a length dimension, and a depth dimension which are slightly larger than a corresponding length, width, and depth of body 12 to allow removably secure positioning of wrench 10 within the docking cavity 1108. A coupling or junction (not shown) is also provided along an interior wall of docking cavity 1108 for electrically connecting control unit 1100 to microcontroller 92 in the body 12. Connection between the control unit 1100 and wrench 10 may also be via a wire 1112 extending between connectors 1114 on the wrench 10 and on the unit 1100 wireless communication when control unit 1100 and wrench 10 are brought in close proximity.

Control units may also be commonly available portable digital assistants or PDA such as those available from Palm, or other mobile computing devices. Software configured to communicate with wrench 10 may be loaded onto the PDA which can use operating systems such as Palm OS, Microsoft Windows CE, or other mobile computing device operating systems presently available or hereafter devised. The communications and operations protocols used by the tool may also be written in HTML or XML programming language, or other suitable systems presently available or hereafter devised for interoperability with a wide range of software and hardware platforms.

The control unit 1100 can be in the form of an Ethernet cradle which is similar to the cradle bundled with most hand held devices. However, such an Ethernet cradle may be designed to include an Ethernet card and an RJ-45 connector. This connector allows the unit to connect to a local area network via a CAT5 cable attached to a hub or switch. This will allow for rapid communication (10 Mbps, 100 MBps, or gigabit) between the wrench 10 and a tool management system 1200.

Figure 19A:
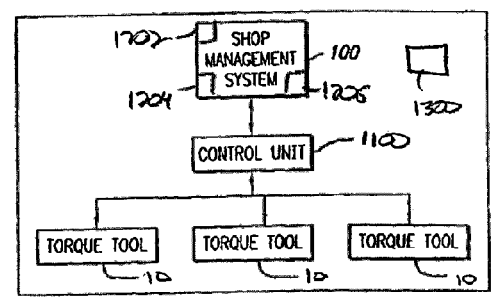
FIG. 19 is a schematic view illustrating the operation of the tool of FIG. 17.
Figure 19B:
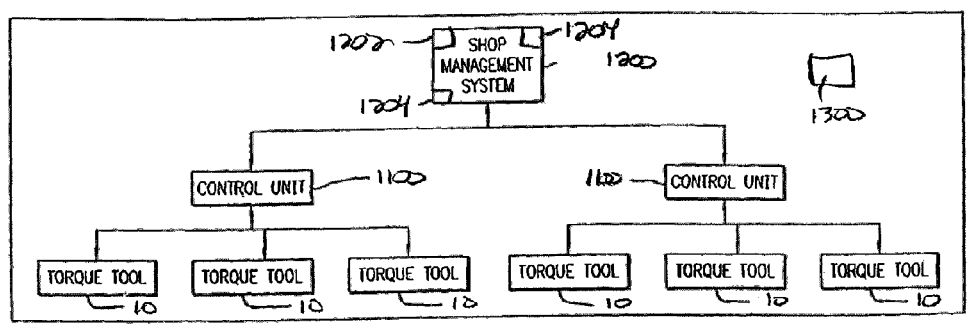

FIGS. 19A-19B are simplified diagrammatic views of a tool management system 1200. Tool management system 1200 can be configured on a general purpose computer that includes a processor 1202, a specification database module 1204 accessible by or loaded onto the system 1200, a database module 1206 accessible by or loaded onto system 100, and a communications port 1208. The modules 1204, 1206 can be accessed by the processor locally or remotely over a communications network such as a local area network, wide area network, over an intranet, or over the Internet or another suitable communications hereafter devised and usable for this system. Tool management system 1200 will also include both dynamic memory such as RAM and a storage device such as a hard drive or the like. The term "module" referenced in this disclosure is meant to broadly cover various types of software code including but not limited to routines, functions, objects, libraries, classes, members, packages, procedures, methods, or lines of code together performing similar functionality to these types of coding, therefore one program can operate to provides the functionality, or the functionality can be divided over a number of programs, accessible either locally or remotely. The system 1200 may also communicate with one or more output devices 1300 such as monitors or printers. For the purposes of the present example, and as illustrated in figures, the database modules 1204, 1206 will be loaded on the tool management system 1200.

The tool management system 1200 can communicate directly with wrench 10. System 1200 and wrench 10 make up torque management system. This connection may be via a hardwired or wireless using any of the communications protocols previously described. In an alternative embodiment, the control unit 1200 can also be used an intermediate interface between tool management system 1200 and wrench 10 to form the torque management system 1400. The control unit 1100 can also be used to control more than one wrench 10. Recall that wrench 10 removably docks with control unit 1100 so one wrench 10 can be removed and another connected so that one control unit 1100 can be used to communicate with more than one wrench 10.

The general steps by which tool/torque management system 1200/1400 are used initially involve the identification of a torque application, can be any task or process that requires the use of a torque tool where precise tolerances, a desired range, or limits of the magnitude of the torque applied need to be monitored. Generally, a fastening or unfastening of a fastener to a member can be a torque application. One specific example of a torque application is related to inserting screws into a plate in a human body during a surgical procedure. In this example, a number of screws need to be inserted through the plate into bone in order to secure the plate where desired within the body, e.g., to repair a break in a bone. It is known in the medical device/fastener industry that each manufacturer offers specifications for a recommended and maximum safe amount of torque that should be applied to securely fasten the screws.

Once selected, the information on the torque application is supplied from a database 1204, 1206 on the system 1200 to the wrench 10, and/or to the control unit 1100. In doing so, the system 1200 references the specifications database module 1206 to find corresponding manufacturer's specifications for the identified torque application. Alternatively, the fastener (not shown) can have a code used to identify the fastener with system 1200. The identification to the system 1200 can be made via the wrench 10, the system 1200, or the control unit 110 using any input method or device including using a keyboard, interacting with a graphical user interface that has menus or other selection protocols, scanning a barcode, or from import/export or other communication with procedure database.

Once identified, the manufacturer's specifications for the identified torque application are retrieved to the wrench 10. If the system 1200 referenced the specification database 1206, then the specification are transmitted from the system 1200 to the wrench 10 via a communications path. Alternatively, the system 1200 sends the specifications to the control unit 1100 which in turn transmits the specifications to the wrench 10 when the wrench 10 is docked therein. If the specifications are already on wrench 10, for example because the same torque application was performed prior to the current torque application, the specification can be recalled from the memory 800 of the wrench 10. Similarly, if the specifications are already resident on the control unit 1100, the specifications can be recalled and loaded onto wrench 10.

After loading the specifications on the wrench 10, a user or operator, such as, for example, physician, uses the wrench 10 loaded with the torque application specifications to perform the torque application. The wrench 10 or the wrench 10-control unit 1100 combination are configured to guide the user through the torque application. This guidance can come in the form of specifying a particular portion of the application and displaying a maximum allowable applied torque. The torque magnitudes displayed can be in either U.S. customary units (lbs-ft) or in S.I. units (N-m). The guidance can also come in the form of producing an alert during torque application to notify the user that the user is approaching or has exceeded a specification, such as the LEDs 88a-88c, the speaker 90 or other devices mentioned previously.

Generally simultaneously with the guidance process described above and the various steps of the torque application, a torque sensing device within the wrench 10 measures or captures data corresponding to the actual torque applied for that application. That information or data is stored in memory 800 within the wrench 10 or is immediately transmitted back to the control unit 1100 or directly to the tool management system 1200. The data is used to create a record of exactly how much torque was applied during the various stages of the torque application, and how long the wrench 10 was in use. In an embodiment where the data is not immediately transmitted from the wrench 10, the data can be retrieved and sent to the control unit 1100 and system 1200 during docking.

The specifications and other torque-related information in the specifications database module 1204 can be compiled from promulgated industry standards or from specification released by original equipment manufacturers. For example, factory torque specifications developed by the device manufacturer relating to the proper torque for tightening the fasteners can be maintained in the database 1204. The information can be modified, updated and corrected as necessary. If this system 1200 is connected to a network that has access to updated specifications, this information update can occur at generally any time of the day.

In order to maintain system integrity and security, the various steps described above may include password system implementation or user authentication for added security and user accountability. For example, a physician performing a torque application may have to enter a worker ID. As another example, specifications updates to the specification database module 1204 may require manager level access.

Figure 20:
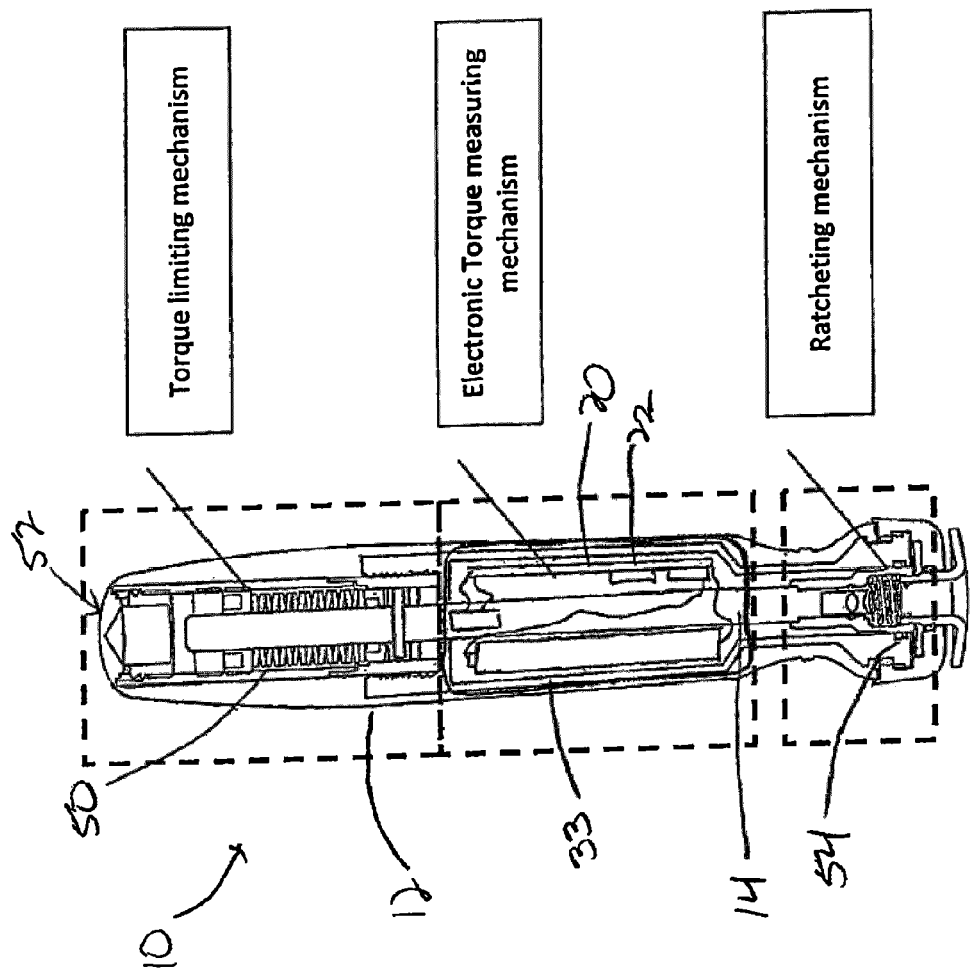
FIG. 20 is a cross-sectional view of a seventh embodiment of an electronic driving tool constructed according to the present disclosure.

Looking now at FIG. 20, a seventh embodiment of the present invention is illustrated in which the electronic torque wrench 10" includes a wrench body 12", a ratchet/wrench shaft 14", and a battery assembly 19", and an electronics unit 20" with a user interface or display 22" disposed within the body 12" engaged with a sensor 30" on the shaft 14". A torque limiting mechanism 50", such as that disclosed in U.S. Pat. No. 7,430,945, which expressly is incorporated herein by reference in its entirety, is disposed within and at one end 52" of the wrench body 12", and a ratcheting mechanism 54" is located opposite the mechanism 50", with both mechanisms 50" and 54" operably connected to the shaft 14".

Figure 21:
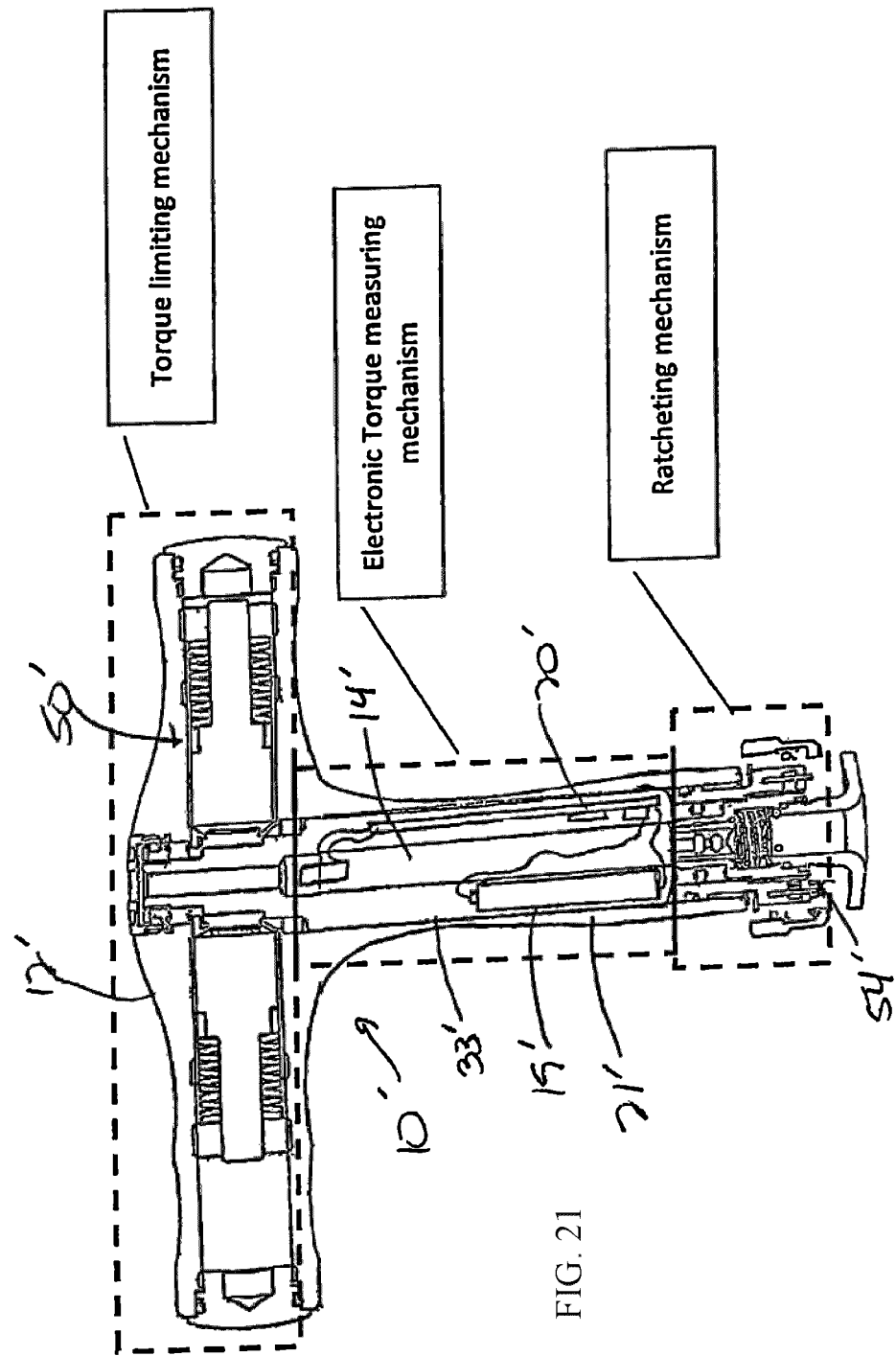
FIG. 21 is a cross-sectional view of an eighth embodiment of an electronic driving tool constructed according to the present disclosure.

Referring now to FIG. 21, an eighth embodiment of the present invention is illustrated where the wrench 10''' has a T-shape, with the shaft 14''' extending perpendicularly from the body 12'''. In the illustrated embodiment, the shaft 14''' is disposed centrally on the body 12''', such that the battery assembly or power source 19''' and the electronics unit 20''' operably connected to the shaft 14''' via the sensor 30''' are disposed around the shaft 14''' within a housing 21''' connected to and extending perpendicularly from the body 12''. The housing 21''' is connected to the body 12''' and the shaft 14''' can be connected directly to the body 12''' or to a torque limiting mechanism 50''', such as that disclosed in U.S. Pat. No. 7,430,945, which expressly is incorporated herein by reference in its entirety, disposed within the body 12'''. In addition, the disposed at least partially within the housing 21''' and in connection with the shaft 14''' is a ratcheting mechanism 54''' as previously described with regard to the embodiment of FIGS. 1 and 2. Further, in this, or any other embodiment of the wrench 10, 10', 10'' or 10''', the wrench can include a ratcheting mechanism 54, a mechanical torque limiting mechanism 50, or a mechanical torque measuring mechanism, such as the mechanical torque level measuring and/or indication mechanism 570, or any combination thereof in addition to the other components of any disclosed embodiment of the electronic torque wrench 10, 10', 10'' or 10'''.

Figure 22:
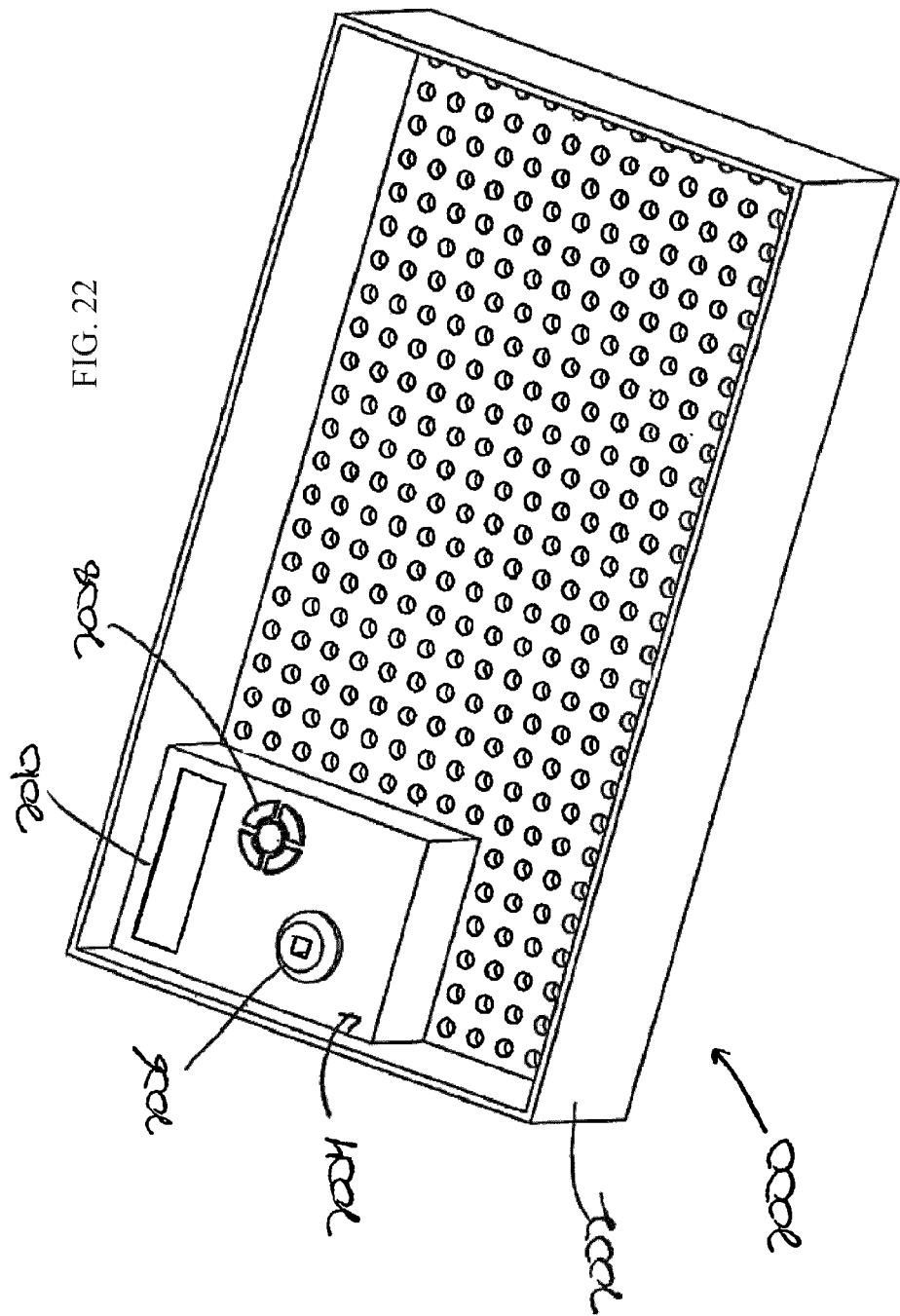
FIG. 22 is an isometric view of a calibration tray used with the electronic driving tool.
Figure 23:
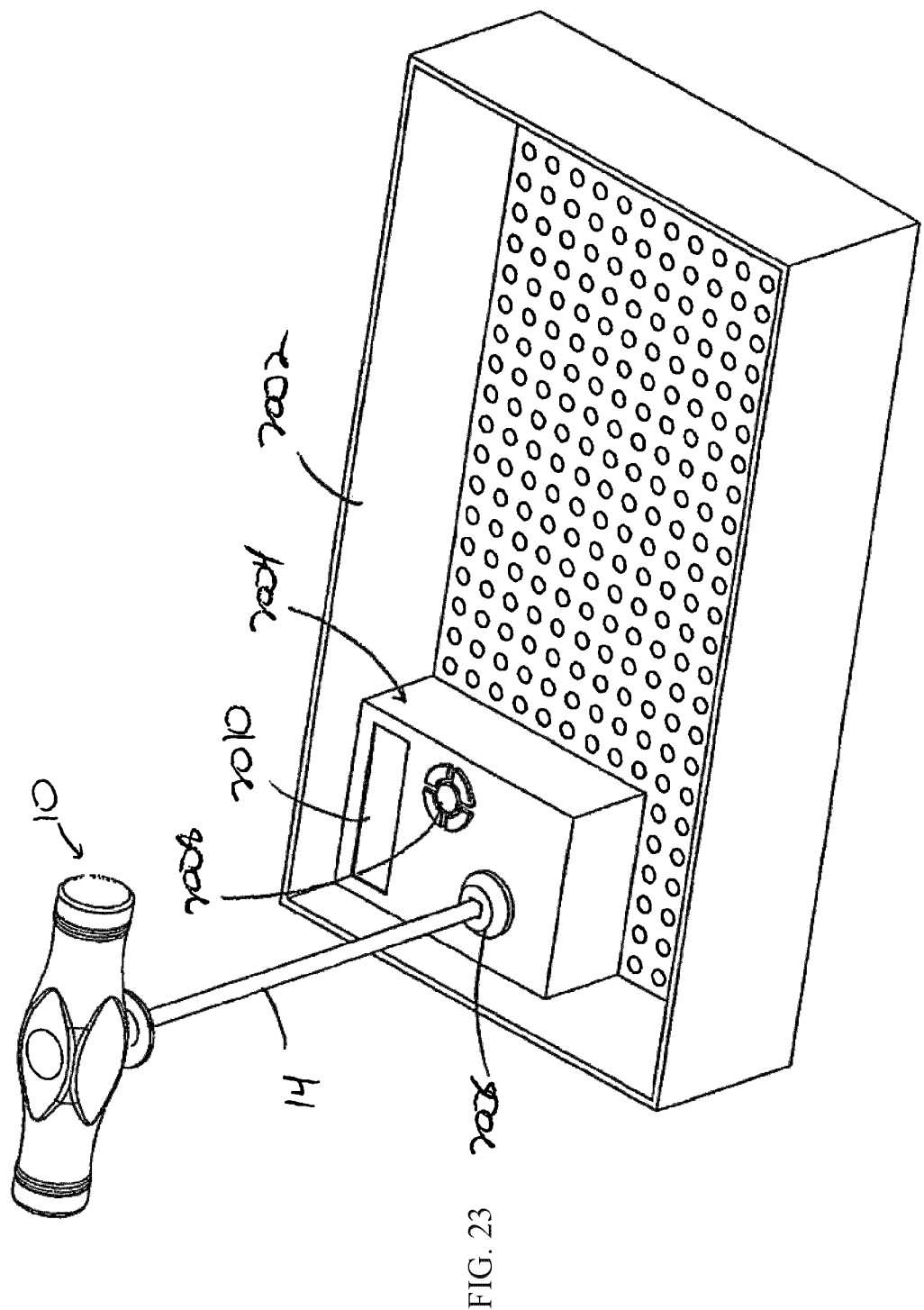
FIG. 23 is an isometric view of a driving tool constructed according to the present disclosure utilized with the calibration tray of FIG. 22.
Figure 24:
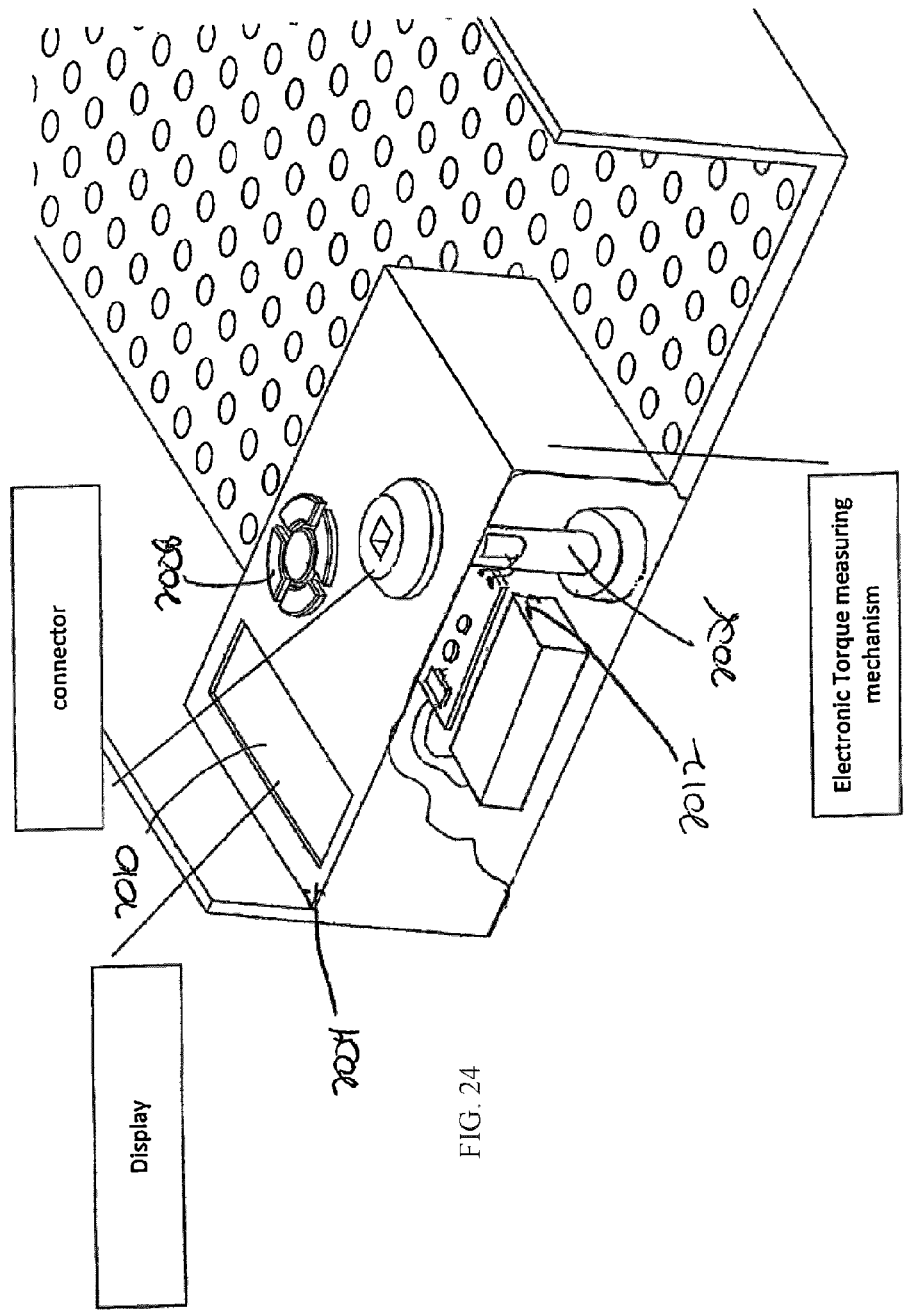
FIG. 24 is a partially broken away, isometric view of the calibration tray of FIG. 22.

Referring now to FIGS. 22-24, a calibration tray 2000 is illustrated for use with the wrench 10 of the present invention. The tray 2000 includes an enclosure 2002 within which the wrench 10 or other tool can be initially packaged, along with other suitable attachments or devices (not shown) for use with the wrench 10. The enclosure 2002 also houses a calibration device 2004 therein. The device 2004 includes a connector port 2006 for engagement with the shaft 14 of the wrench 10, a number of operational buttons 2008 to control the operation of the device 2004, and a display 2010 for providing a visual representation of the output of the device 2004 to the user. The connector 2006 is operably connected to a torque-measuring device 2012 disposed within the device 2004, and capable of determining the torque applied to the connector port 206 by the wrench 10, and providing an output of the torque value determined via the display 2010. By engaging the wrench 10 with the device 2004 and measuring the torque applied by the wrench 10 on the wrench 10 and on the device 2004, it is possible to determine if the wrench 10 needs any adjustment in order to have the torque level measured by the wrench 10 match the level measured by the device 2004.

In other alternative embodiments, the battery assembly/power source 19 for the wrench 10 can be formed to be removable as a unit from the wrench 10 similarly to the embodiment in FIG. 7. The battery assembly/power source 19 is initially formed as a sterile component that can be secured to the wrench 10 to supply power thereto, and optionally to form a part of the barrier 33 or that can be separate from the barrier 33. In circumstances where the wrench 10 is dropped or where the wrench 10 is stored for a significant period of time, the power source 19 can be removed from the wrench 10 and the wrench 10 can be autoclaved. A new, sterile power source 19 can then be engaged with the wrench 10 to provide power to the wrench 10.

While the concepts of the present disclosure will be illustrated and described in detail in the drawings and description, such an illustration and description is to be considered as exemplary and not restrictive in character, it being understood that only the illustrative embodiments are shown and described and that all changes and modifications that come within the spirit of the disclosure are desired to be protected. There are a plurality of advantages that may be inferred from the present disclosure arising from the various features of the apparatus, systems, and methods described herein. It will be noted that alternative embodiments of each of the apparatus, systems, and methods of the present disclosure may not include all of the features described yet still benefit from at least some of the inferred advantages of such features. Those of ordinary skill in the art may readily devise their own implementations of an apparatus, system, and method that incorporate one or ore of the features of the present disclosure and fall within the spirit and scope of the disclosure as defined by the appended claims.

The invention claimed is:

1. A torque wrench comprising:
   a) a body;
   b) a shaft extending from the body and engageable with a fastener;
   c) an electronics unit positioned within the body and operably connected to the shaft, the electronics unit operable to measure the torque exerted though the shaft on a fastener and including a circuit board and a power source; and
   d) a barrier positioned around the electronics unit to isolate the electronics unit from an exterior environment of the wrench to enable the electronics unit to be subjected to sterilizing environments when inserted within the body or separate from the body without causing damage to the electronics unit.

2. The wrench of claim 1 further comprising a display disposed on the body within the barrier and operably connected to the electronics unit.

3. The wrench of claim 1 further comprising a display disposed on the body and forming a portion of the barrier the barrier wherein the display is operably connected to the electronics unit within the barrier.

4. The wrench of claim 1 further comprising at least one switch operably connected to the electronics unit and disposed at least partially on the exterior of the barrier.

5. The wrench of claim 1 further comprising a light source disposed on the body adjacent the shaft to selectively illuminate an end of the shaft spaced from the body.

6. The wrench of claim 1 wherein the wrench is an in-line wrench or a right angle wrench.

7. The wrench of claim 1 wherein the wrench is a T-handle wrench.

8. The wrench of claim 1 further comprising at least one of a ratcheting mechanism, a mechanical torque limiting mechanism, a mechanical torque measuring mechanism, or any combination thereof.

9. The wrench of claim 1 wherein the electronics unit is sterile prior to insertion into the body.

10. A method of tightening a fastener comprising the steps of:
    a) providing the electronic torque wrench of claim 1;
    b) engaging the wrench with the fastener; and
    c) turning the wrench to tighten the fastener until the desired torque level is reached.

11. The wrench of claim 1 further comprising a power source disposed within the body and operably connected to the electronics unit.

12. The wrench of claim 11 wherein the power source forms a part of the barrier positioned around the electronics unit.

13. A method of tightening a fastener comprising the steps of:
    a) providing the electronic torque wrench of claim 11 wherein the power source is removable from the body;
    b) engaging the wrench with the fastener;

c) turning the wrench to tighten the fastener until the desired torque level is reached;

d) removing a depleted power source from the body; and e) inserting a fresh power source into the body.

14. The wrench of claim 11 wherein the wrench is disposed of after depletion of the power source.

15. The wrench of claim 11 wherein the power source is rechargeable.

* * * * *

UNITED STATES PATENT AND TRADEMARK OFFICE
CERTIFICATE OF CORRECTION

PATENT NO. : 8,714,058 B2
APPLICATION NO. : 13/915395
DATED : May 6, 2014
INVENTOR(S) : Michael T. Gauthier et al.

It is certified that error appears in the above-identified patent and that said Letters Patent is hereby corrected as shown below:

IN THE CLAIMS

Claim 1, column 16, line 19, delete "though" and substitute therefore -- through --.

Signed and Sealed this
Twelfth Day of August, 2014

Michelle K. Lee
*Deputy Director of the United States Patent and Trademark Office*